United States Patent
Misener

(10) Patent No.: US 11,877,810 B2
(45) Date of Patent: Jan. 23, 2024

(54) SYSTEM, METHOD AND APPARATUS FOR MAGNETIC TRACKING OF ULTRASOUND PROBE AND GENERATION OF 3D VISUALIZATION THEREOF

(71) Applicant: Bard Access Systems, Inc., Salt Lake City, UT (US)

(72) Inventor: Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/380,767

(22) Filed: Jul. 20, 2021

(65) Prior Publication Data

US 2022/0022969 A1    Jan. 27, 2022

Related U.S. Application Data

(60) Provisional application No. 63/054,622, filed on Jul. 21, 2020.

(51) Int. Cl.
*A61B 17/34*        (2006.01)
*A61B 34/20*        (2016.01)
(Continued)

(52) U.S. Cl.
CPC ............ *A61B 34/20* (2016.02); *A61B 8/0891* (2013.01); *A61B 8/12* (2013.01); *A61B 8/4263* (2013.01);
(Continued)

(58) Field of Classification Search
CPC ......... A61B 34/20; A61B 8/0891; A61B 8/12; A61B 8/4263; A61B 8/483; A61B 8/488;
(Continued)

(56) References Cited

U.S. PATENT DOCUMENTS 5,148,809 A    9/1992    Biegeleisen-Knight et al.
5,181,513 A    1/1993    Touboul et al.
(Continued)

FOREIGN PATENT DOCUMENTS

AU    2006201646 A1    11/2006
CN       114129137 B     9/2022
(Continued)

OTHER PUBLICATIONS

EZono, eZSimulator, https://www.ezono.com/en/ezsimulator/, last accessed Sep. 13, 2022.
(Continued)

*Primary Examiner* — Serkan Akar
*Assistant Examiner* — Amal Aly Farag
(74) *Attorney, Agent, or Firm* — Rutan & Tucker LLP

(57) ABSTRACT

Disclosed herein is a magnetic-based tracking system for tracking an ultrasound probe to create a three-dimensional visualization. The system includes a reference device including a reference magnet; an ultrasound probe including an ultrasound acoustic transducer or acoustic array that acquires ultrasound images and a magnetometer that detects a magnetic field generated by the reference magnet. The ultrasound probe couples a first ultrasound image with a first magnetic field strength, wherein both of the first ultrasound image is received and the first magnetic field strength is detected at a first time; and a console including a processor and non-transitory computer-readable medium having stored thereon a plurality of processor executed logic modules that perform operations including receiving and recording a plurality of coupling of ultrasound images and detected magnetic field strengths, and generating the 3D visualization from the ultrasound images by aligning the ultrasound images in accordance with a corresponding detected magnetic field strength.

11 Claims, 12 Drawing Sheets

(51) Int. Cl.
  *A61B 8/00* (2006.01)
  *A61B 8/12* (2006.01)
  *A61B 8/08* (2006.01)
  *A61B 90/00* (2016.01)

(52) U.S. Cl.
  CPC .............. *A61B 8/483* (2013.01); *A61B 8/488* (2013.01); *A61B 17/3403* (2013.01); *A61B 2034/2051* (2016.02); *A61B 2090/365* (2016.02)

(58) Field of Classification Search
  CPC ........ A61B 17/3403; A61B 2034/2051; A61B 2090/365
  See application file for complete search history.

(56) References Cited

U.S. PATENT DOCUMENTS

| | | | |
|---|---|---|---|
| 5,325,293 A | 6/1994 | Dorne | |
| 5,441,052 A | 8/1995 | Miyajima | |
| 5,549,554 A | 8/1996 | Miraki | |
| 5,573,529 A | 11/1996 | Haak et al. | |
| 5,775,322 A | 7/1998 | Silverstein et al. | |
| 5,879,297 A | 3/1999 | Haynor et al. | |
| 5,908,387 A | 6/1999 | LeFree et al. | |
| 5,967,984 A | 10/1999 | Chu et al. | |
| 5,970,119 A | 10/1999 | Hofmann | |
| 6,004,270 A | 12/1999 | Urbano et al. | |
| 6,019,724 A | 2/2000 | Gronningsaeter et al. | |
| 6,068,599 A | 5/2000 | Saito et al. | |
| 6,074,367 A | 6/2000 | Hubbell | |
| 6,129,668 A | 10/2000 | Haynor et al. | |
| 6,132,379 A | 10/2000 | Patacsil et al. | |
| 6,216,028 B1 | 4/2001 | Haynor et al. | |
| 6,233,476 B1 | 5/2001 | Strommer et al. | |
| 6,245,018 B1 | 6/2001 | Lee | |
| 6,263,230 B1 | 7/2001 | Haynor et al. | |
| 6,375,615 B1 | 4/2002 | Flaherty et al. | |
| 6,436,043 B2 | 8/2002 | Bonnefous | |
| 6,498,942 B1 | 12/2002 | Esenaliev et al. | |
| 6,503,205 B2 | 1/2003 | Manor et al. | |
| 6,508,769 B2 | 1/2003 | Bonnefous | |
| 6,511,458 B2 | 1/2003 | Milo et al. | |
| 6,524,249 B2 | 2/2003 | Moehring et al. | |
| 6,543,642 B1 | 4/2003 | Milliorn | |
| 6,554,771 B1 | 4/2003 | Buil et al. | |
| 6,592,520 B1 | 7/2003 | Peszynski et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,623,431 B1 | 9/2003 | Sakuma et al. | |
| 6,641,538 B2 | 11/2003 | Nakaya et al. | |
| 6,647,135 B2 | 11/2003 | Bonnefous | |
| 6,687,386 B1 | 2/2004 | Ito et al. | |
| 6,749,569 B1 | 6/2004 | Pellegretti | |
| 6,754,608 B2 | 6/2004 | Svanerudh et al. | |
| 6,755,789 B2 | 6/2004 | Stringer et al. | |
| 6,840,379 B2 | 1/2005 | Franks-Farah et al. | |
| 6,857,196 B2 | 2/2005 | Dalrymple | |
| 6,979,294 B1 | 12/2005 | Selzer et al. | |
| 7,074,187 B2 | 7/2006 | Selzer et al. | |
| 7,244,234 B2 | 7/2007 | Ridley et al. | |
| 7,359,554 B2 | 4/2008 | Klingensmith et al. | |
| 7,534,209 B2 | 5/2009 | Abend et al. | |
| 7,599,730 B2 | 10/2009 | Hunter et al. | |
| 7,637,870 B2 | 12/2009 | Flaherty et al. | |
| 7,681,579 B2 | 3/2010 | Schwartz | |
| 7,691,061 B2 | 4/2010 | Hirota | |
| 7,699,779 B2 | 4/2010 | Sasaki et al. | |
| 7,720,520 B2 | 5/2010 | Willis | |
| 7,727,153 B2 | 6/2010 | Fritz et al. | |
| 7,734,326 B2 | 6/2010 | Pedain et al. | |
| 7,831,449 B2 | 11/2010 | Ying et al. | |
| 7,905,837 B2 | 3/2011 | Suzuki | |
| 7,925,327 B2 | 4/2011 | Weese | |
| 7,927,278 B2 | 4/2011 | Selzer et al. | |
| 8,014,848 B2 | 9/2011 | Birkenbach et al. | |
| 8,050,523 B2 | 11/2011 | Younge et al. | |
| 8,060,181 B2 | 11/2011 | Rodriguez Ponce et al. | |
| 8,068,581 B2 | 11/2011 | Boese et al. | |
| 8,075,488 B2 | 12/2011 | Burton | |
| 8,090,427 B2 | 1/2012 | Eck et al. | |
| 8,105,239 B2 | 1/2012 | Specht | |
| 8,172,754 B2 | 5/2012 | Watanabe et al. | |
| 8,175,368 B2 | 5/2012 | Sathyanarayana | |
| 8,200,313 B1 | 6/2012 | Rambod et al. | |
| 8,211,023 B2 | 7/2012 | Swan et al. | |
| 8,228,347 B2 | 7/2012 | Beasley et al. | |
| 8,298,147 B2 | 10/2012 | Huennekens et al. | |
| 8,303,505 B2 | 11/2012 | Webler et al. | |
| 8,323,202 B2 | 12/2012 | Roschak et al. | |
| 8,328,727 B2 | 12/2012 | Miele et al. | |
| 8,388,541 B2 | 3/2013 | Messerly et al. | |
| 8,409,103 B2 | 4/2013 | Grunwald et al. | |
| 8,449,465 B2 | 5/2013 | Nair et al. | |
| 8,553,954 B2 | 10/2013 | Saikia | |
| 8,556,815 B2 | 10/2013 | Pelissier et al. | |
| 8,585,600 B2 | 11/2013 | Liu et al. | |
| 8,622,913 B2 | 1/2014 | Dentinger et al. | |
| 8,706,457 B2 | 4/2014 | Hart et al. | |
| 8,727,988 B2 | 5/2014 | Flaherty et al. | |
| 8,734,357 B2 | 5/2014 | Taylor | |
| 8,744,211 B2 | 6/2014 | Owen | |
| 8,754,865 B2 | 6/2014 | Merritt et al. | |
| 8,764,663 B2 | 7/2014 | Smok et al. | |
| 8,781,194 B2 | 7/2014 | Malek et al. | |
| 8,781,555 B2 | 7/2014 | Burnside et al. | |
| 8,790,263 B2 | 7/2014 | Randall et al. | |
| 8,849,382 B2 | 9/2014 | Cox et al. | |
| 8,939,908 B2 | 1/2015 | Suzuki et al. | |
| 8,961,420 B2 | 2/2015 | Zhang | |
| 9,022,940 B2 | 5/2015 | Meier | |
| 9,138,290 B2 | 9/2015 | Hadjicostis | |
| 9,155,517 B2 | 10/2015 | Dunbar et al. | |
| 9,204,858 B2 | 12/2015 | Pelissier et al. | |
| 9,220,477 B2 | 12/2015 | Urabe et al. | |
| 9,257,220 B2 | 2/2016 | Nicholls et al. | |
| 9,295,447 B2 | 3/2016 | Shah | |
| 9,320,493 B2 | 4/2016 | Visveshwara | |
| 9,357,980 B2 | 6/2016 | Toji et al. | |
| 9,364,171 B2 | 6/2016 | Harris et al. | |
| 9,427,207 B2 | 8/2016 | Sheldon et al. | |
| 9,445,780 B2 | 9/2016 | Hossack et al. | |
| 9,456,766 B2 | 10/2016 | Cox et al. | |
| 9,456,804 B2 | 10/2016 | Tamada | |
| 9,459,087 B2 | 10/2016 | Dunbar et al. | |
| 9,468,413 B2 | 10/2016 | Hall et al. | |
| 9,492,097 B2 | 11/2016 | Wilkes et al. | |
| 9,521,961 B2 | 12/2016 | Silverstein et al. | |
| 9,554,716 B2 | 1/2017 | Burnside et al. | |
| 9,582,876 B2 | 2/2017 | Specht | |
| 9,597,008 B2 | 3/2017 | Henkel et al. | |
| 9,610,061 B2 | 4/2017 | Ebbini et al. | |
| 9,636,031 B2 | 5/2017 | Cox | |
| 9,649,037 B2 | 5/2017 | Lowe et al. | |
| 9,649,048 B2 | 5/2017 | Cox et al. | |
| 9,702,969 B2 | 7/2017 | Hope Simpson et al. | |
| 9,715,757 B2 | 7/2017 | Ng et al. | |
| 9,717,415 B2 | 8/2017 | Cohen et al. | |
| 9,731,066 B2 | 8/2017 | Liu et al. | |
| 9,814,433 B2 | 11/2017 | Benishti et al. | |
| 9,814,531 B2 | 11/2017 | Yagi et al. | |
| 9,861,337 B2 | 1/2018 | Patwardhan et al. | |
| 9,895,138 B2 | 2/2018 | Sasaki | |
| 9,913,605 B2 | 3/2018 | Harris et al. | |
| 9,949,720 B2 | 4/2018 | Southard et al. | |
| 10,043,272 B2 | 8/2018 | Forzoni et al. | |
| 10,380,919 B2 | 8/2019 | Savitsky et al. | |
| 10,380,920 B2 | 8/2019 | Savitsky et al. | |
| 10,424,225 B2 | 9/2019 | Nataneli et al. | |
| 10,434,278 B2 | 10/2019 | Dunbar et al. | |
| 10,449,330 B2 | 10/2019 | Newman et al. | |
| 10,524,691 B2 | 1/2020 | Newman et al. | |

(56) References Cited

U.S. PATENT DOCUMENTS

| | | |
|---|---|---|
| 10,674,935 B2 | 6/2020 | Henkel et al. |
| 10,751,509 B2 | 8/2020 | Misener |
| 10,758,155 B2 | 9/2020 | Henkel et al. |
| 10,765,343 B2 | 9/2020 | Henkel et al. |
| 10,896,628 B2 | 1/2021 | Savitsky et al. |
| 11,062,624 B2 | 7/2021 | Savitsky et al. |
| 11,120,709 B2 | 9/2021 | Savitsky et al. |
| 11,311,269 B2 | 4/2022 | Dunbar et al. |
| 11,315,439 B2 | 4/2022 | Savitsky et al. |
| 11,600,201 B1 | 3/2023 | Savitsky et al. |
| 2002/0038088 A1 | 3/2002 | Imran et al. |
| 2002/0148277 A1 | 10/2002 | Umeda |
| 2003/0047126 A1 | 3/2003 | Tomaschko |
| 2003/0060714 A1 | 3/2003 | Henderson et al. |
| 2003/0073900 A1* | 4/2003 | Senarith ............ A61B 90/36 600/585 |
| 2003/0093001 A1* | 5/2003 | Martikainen ......... A61B 5/022 600/499 |
| 2003/0106825 A1 | 6/2003 | Molina et al. |
| 2003/0120154 A1 | 6/2003 | Sauer et al. |
| 2004/0055925 A1 | 3/2004 | Franks-Farah et al. |
| 2005/0000975 A1 | 1/2005 | Carco et al. |
| 2005/0049504 A1 | 3/2005 | Lo et al. |
| 2005/0165299 A1 | 7/2005 | Kressy et al. |
| 2005/0251030 A1 | 11/2005 | Azar et al. |
| 2005/0267365 A1 | 12/2005 | Sokulin et al. |
| 2006/0013523 A1 | 1/2006 | Childlers et al. |
| 2006/0015039 A1 | 1/2006 | Cassidy et al. |
| 2006/0079781 A1 | 4/2006 | Germond-Rouet et al. |
| 2006/0184029 A1 | 8/2006 | Haim et al. |
| 2006/0210130 A1 | 9/2006 | Germond-Rouet et al. |
| 2007/0043341 A1 | 2/2007 | Anderson et al. |
| 2007/0049822 A1 | 3/2007 | Bunce et al. |
| 2007/0073155 A1 | 3/2007 | Park et al. |
| 2007/0199848 A1 | 8/2007 | Ellswood et al. |
| 2007/0239120 A1 | 10/2007 | Brock et al. |
| 2007/0249911 A1 | 10/2007 | Simon |
| 2008/0021322 A1 | 1/2008 | Stone et al. |
| 2008/0033293 A1 | 2/2008 | Beasley et al. |
| 2008/0033759 A1 | 2/2008 | Finlay |
| 2008/0051657 A1 | 2/2008 | Rold |
| 2008/0146915 A1 | 6/2008 | McMorrow |
| 2008/0177186 A1 | 7/2008 | Slater et al. |
| 2008/0221425 A1 | 9/2008 | Olson et al. |
| 2008/0294037 A1 | 11/2008 | Richter |
| 2008/0300491 A1 | 12/2008 | Bonde et al. |
| 2009/0012399 A1 | 1/2009 | Sunagawa et al. |
| 2009/0143672 A1 | 6/2009 | Harms et al. |
| 2009/0143684 A1 | 6/2009 | Cermak et al. |
| 2009/0156926 A1 | 6/2009 | Messerly et al. |
| 2009/0306509 A1 | 12/2009 | Pedersen et al. |
| 2010/0020926 A1 | 1/2010 | Boese et al. |
| 2010/0106015 A1 | 4/2010 | Norris |
| 2010/0211026 A2 | 8/2010 | Sheetz et al. |
| 2010/0277305 A1 | 11/2010 | Garner et al. |
| 2010/0286515 A1 | 11/2010 | Gravenstein et al. |
| 2010/0312121 A1 | 12/2010 | Guan |
| 2011/0002518 A1 | 1/2011 | Ziv-Ari et al. |
| 2011/0071404 A1 | 3/2011 | Schmitt et al. |
| 2011/0295108 A1 | 12/2011 | Cox et al. |
| 2011/0313293 A1 | 12/2011 | Lindekugel et al. |
| 2012/0179038 A1 | 7/2012 | Meurer et al. |
| 2012/0197132 A1 | 8/2012 | O'Connor |
| 2012/0209121 A1 | 8/2012 | Boudier |
| 2012/0220865 A1 | 8/2012 | Brown et al. |
| 2012/0238875 A1* | 9/2012 | Savitsky ............ G09B 23/286 600/443 |
| 2012/0277576 A1 | 11/2012 | Lui |
| 2013/0041250 A1 | 2/2013 | Pelissier et al. |
| 2013/0102889 A1 | 4/2013 | Southard et al. |
| 2013/0131499 A1 | 5/2013 | Chan et al. |
| 2013/0131502 A1 | 5/2013 | Blaivas et al. |
| 2013/0150724 A1 | 6/2013 | Blaivas et al. |
| 2013/0188832 A1 | 7/2013 | Ma et al. |
| 2013/0218024 A1 | 8/2013 | Boctor et al. |
| 2013/0324840 A1 | 12/2013 | Zhongping et al. |
| 2014/0005530 A1 | 1/2014 | Liu et al. |
| 2014/0036091 A1 | 2/2014 | Zalev et al. |
| 2014/0073976 A1 | 3/2014 | Fonte et al. |
| 2014/0100440 A1 | 4/2014 | Cheline et al. |
| 2014/0155737 A1 | 6/2014 | Manzke et al. |
| 2014/0180098 A1 | 6/2014 | Flaherty et al. |
| 2014/0188133 A1 | 7/2014 | Misener |
| 2014/0188440 A1 | 7/2014 | Donhowe et al. |
| 2014/0276059 A1 | 9/2014 | Sheehan |
| 2014/0276081 A1 | 9/2014 | Tegels |
| 2014/0276085 A1 | 9/2014 | Miller |
| 2014/0276690 A1 | 9/2014 | Grace |
| 2014/0343431 A1 | 11/2014 | Vajinepalli et al. |
| 2015/0005738 A1 | 1/2015 | Blacker |
| 2015/0011887 A1 | 1/2015 | Ahn et al. |
| 2015/0065916 A1 | 3/2015 | Maguire et al. |
| 2015/0073279 A1 | 3/2015 | Cai et al. |
| 2015/0112200 A1 | 4/2015 | Oberg et al. |
| 2015/0209113 A1 | 7/2015 | Burkholz et al. |
| 2015/0209526 A1 | 7/2015 | Matsubara et al. |
| 2015/0297097 A1 | 10/2015 | Matsubara et al. |
| 2015/0327841 A1 | 11/2015 | Banjanin et al. |
| 2015/0359991 A1 | 12/2015 | Dunbar et al. |
| 2016/0029995 A1 | 2/2016 | Navratil et al. |
| 2016/0113699 A1 | 4/2016 | Sverdlik et al. |
| 2016/0120607 A1 | 5/2016 | Sorotzkin et al. |
| 2016/0143622 A1 | 5/2016 | Xie et al. |
| 2016/0166232 A1 | 6/2016 | Merritt |
| 2016/0202053 A1 | 7/2016 | Walker et al. |
| 2016/0213398 A1 | 7/2016 | Liu |
| 2016/0278743 A1 | 9/2016 | Kawashima |
| 2016/0278869 A1 | 9/2016 | Grunwald |
| 2016/0296208 A1 | 10/2016 | Sethuraman et al. |
| 2016/0374644 A1 | 12/2016 | Mauldin, Jr. et al. |
| 2017/0079548 A1 | 3/2017 | Silverstein et al. |
| 2017/0164923 A1 | 6/2017 | Matsumoto |
| 2017/0172424 A1 | 6/2017 | Eggers et al. |
| 2017/0196535 A1 | 7/2017 | Arai et al. |
| 2017/0215842 A1 | 8/2017 | Ryu et al. |
| 2017/0259013 A1 | 9/2017 | Boyden et al. |
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0225993 A1 | 8/2018 | Buras et al. |
| 2018/0228465 A1 | 8/2018 | Southard et al. |
| 2018/0250078 A1 | 9/2018 | Shochat et al. |
| 2018/0279996 A1 | 10/2018 | Cox et al. |
| 2018/0310955 A1 | 11/2018 | Lindekugel et al. |
| 2018/0317881 A1 | 11/2018 | Astigarraga et al. |
| 2019/0060014 A1 | 2/2019 | Hazelton et al. |
| 2019/0069923 A1 | 3/2019 | Wang |
| 2019/0076121 A1 | 3/2019 | Southard et al. |
| 2019/0088019 A1 | 3/2019 | Prevrhal et al. |
| 2019/0105017 A1 | 4/2019 | Hastings |
| 2019/0117190 A1 | 4/2019 | Djajadiningrat et al. |
| 2019/0282324 A1 | 9/2019 | Freeman et al. |
| 2019/0298457 A1 | 10/2019 | Bharat |
| 2019/0307516 A1 | 10/2019 | Schotzko et al. |
| 2019/0339525 A1 | 11/2019 | Yanof et al. |
| 2019/0365348 A1 | 12/2019 | Toume et al. |
| 2020/0113540 A1 | 4/2020 | Gijsbers et al. |
| 2021/0166583 A1 | 6/2021 | Buras et al. |
| 2021/0307838 A1 | 10/2021 | Xia et al. |
| 2021/0353255 A1 | 11/2021 | Schneider et al. |
| 2021/0402144 A1 | 12/2021 | Messerly |
| 2022/0039685 A1 | 2/2022 | Misener et al. |
| 2022/0039777 A1 | 2/2022 | Durfee |
| 2022/0096797 A1 | 3/2022 | Prince |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |

(56) References Cited

U.S. PATENT DOCUMENTS

| | | |
|---|---|---|
| 2022/0381630 A1 | 12/2022 | Sowards et al. |
| 2023/0113291 A1 | 4/2023 | de Wild et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 3181083 A1 | 6/2017 |
| EP | 3530221 A1 | 8/2019 |
| JP | 2000271136 A | 10/2000 |
| JP | 2014150928 A | 8/2014 |
| JP | 2018175547 A | 11/2018 |
| KR | 20180070878 A | 6/2018 |
| KR | 20190013133 A | 2/2019 |
| NO | 2022/072727 A2 | 4/2022 |
| WO | 2013059714 A1 | 4/2013 |
| WO | 2014/115150 A1 | 7/2014 |
| WO | 2014174305 A2 | 10/2014 |
| WO | 2015/017270 A1 | 2/2015 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2018206473 A1 | 11/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020/186198 A1 | 9/2020 |
| WO | 2022/031762 A1 | 2/2022 |
| WO | 2022/081904 A1 | 4/2022 |
| WO | 2022-203713 A2 | 9/2022 |
| WO | 2022263763 A1 | 12/2022 |

OTHER PUBLICATIONS

Ikhsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XP036387340, ISSN: 1346-4523, DOI: 10.1007/S10396-017-0789-2 [retrieved on Apr. 19, 2017].

PCT/US2021/044419 filed Aug. 3, 2021 International Search Report and Written Opinion dated Nov. 19, 2021.

PCT/US2021/050973 filed Sep. 17, 2021 International Search Report and Written Opinion dated Nov. 7, 2022.

Sonosim, https://sonosim.com/ultrasound-simulation/? last accessed Sep. 13, 2022.

U.S. Appl. No. 17/397,486, filed Aug. 9, 2021 Restriction Requirement dated Aug. 12, 2022.

Lu Zhenyu et al."Recent advances in 5 robot-assisted echography combining perception control and cognition." Cognitive Computation and Systems the Institution of Engineering and Technology, Michael Faraday House, Six Hills Way, Stevenage Herts. SG1 2AY UK vol. 2 No. 3 Sep. 2, 2020 (Sep. 2, 2020).

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/045218 filed Aug. 9, 2021 International Search Report and Written Opinion dated Nov. 23, 2021.

PCT/US2021/053018 filed Sep. 30, 2021 International Search Report and Written Opinion dated May 3, 2022.

PCT/US2021/055076 filed Oct. 14, 2021 International Search Report and Written Opinion dated Mar. 25, 2022.

Sebastian Vogt: "Real-Time Augmented Reality for Image-Guided Interventions", Oct. 5, 2009, XP055354720, Retrieved from the Internet: URL: https://opus4.kobv.de/opus4-fau/frontdoor/deliver/index/docld/1235/file/SebastianVogtDissertation.pdf.

William F Garrett et al: "Real-time incremental visualization of dynamic ultrasound volumes using parallel BSP trees", Visualization '96. Proceedings, IEEE, NE, Oct. 27, 1996, pp. 235-ff, XP058399771, ISBN: 978-0-89791-864-0 abstract, figures 1-7, pp. 236-240.

PCT/US2021/042369 filed Jul. 20, 2021 International Search Report and Written Opinion dated Oct. 25, 2021.

State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).

Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).

U.S. Appl. No. 17/397,486, filed Aug. 9, 2021 Final Office Action dated Aug. 4, 2023.

U.S. Appl. No. 17/491,308, filed Sep. 30, 2021 Non-Final Office Action dated Jun. 5, 2023.

U.S. Appl. No. 17/501,909, filed Oct. 14, 2021 Non-Final Office Action dated Jun. 6, 2023.

U.S. Appl. No. 17/832,389, filed Jun. 3, 2022 Restriction Requirement dated Jul. 13, 2023.

U.S. Appl. No. 17/393,283, filed Aug. 3, 2021 Non-Final Office Action dated Mar. 31, 2023.

U.S. Appl. No. 17/393,283, filed Aug. 3, 2021 Restriction Requirement dated Jan. 12, 2023.

U.S. Appl. No. 17/397,486, filed Aug. 9, 2021 Non-Final Office Action dated Jan. 23, 2023.

U.S. Appl. No. 17/491,308, filed Sep. 30, 2021 Restriction Requirement dated Feb. 27, 2023.

U.S. Appl. No. 17/501,909, filed Oct. 14, 2021 Restriction Requirement dated Feb. 1, 2023.

PCT/US2023/024067 filed May 31, 2023 International Search Report and Written Opinion dated Sep. 15, 2023.

U.S. Appl. No. 17/397,486, filed Aug. 9, 2021 Advisory Action dated Oct. 5, 2023.

U.S. Appl. No. 17/491,308, filed Sep. 30, 2021 Final Office Action dated Aug. 29, 2023.

U.S. Appl. No. 17/832,389, filed Jun. 3, 2022 Non-Final Office Action dated Oct. 6, 2023.

U.S. Appl. No. 17/861,031, filed Jul. 8, 2022 Non-Final Office Action dated Sep. 14, 2023.

* cited by examiner

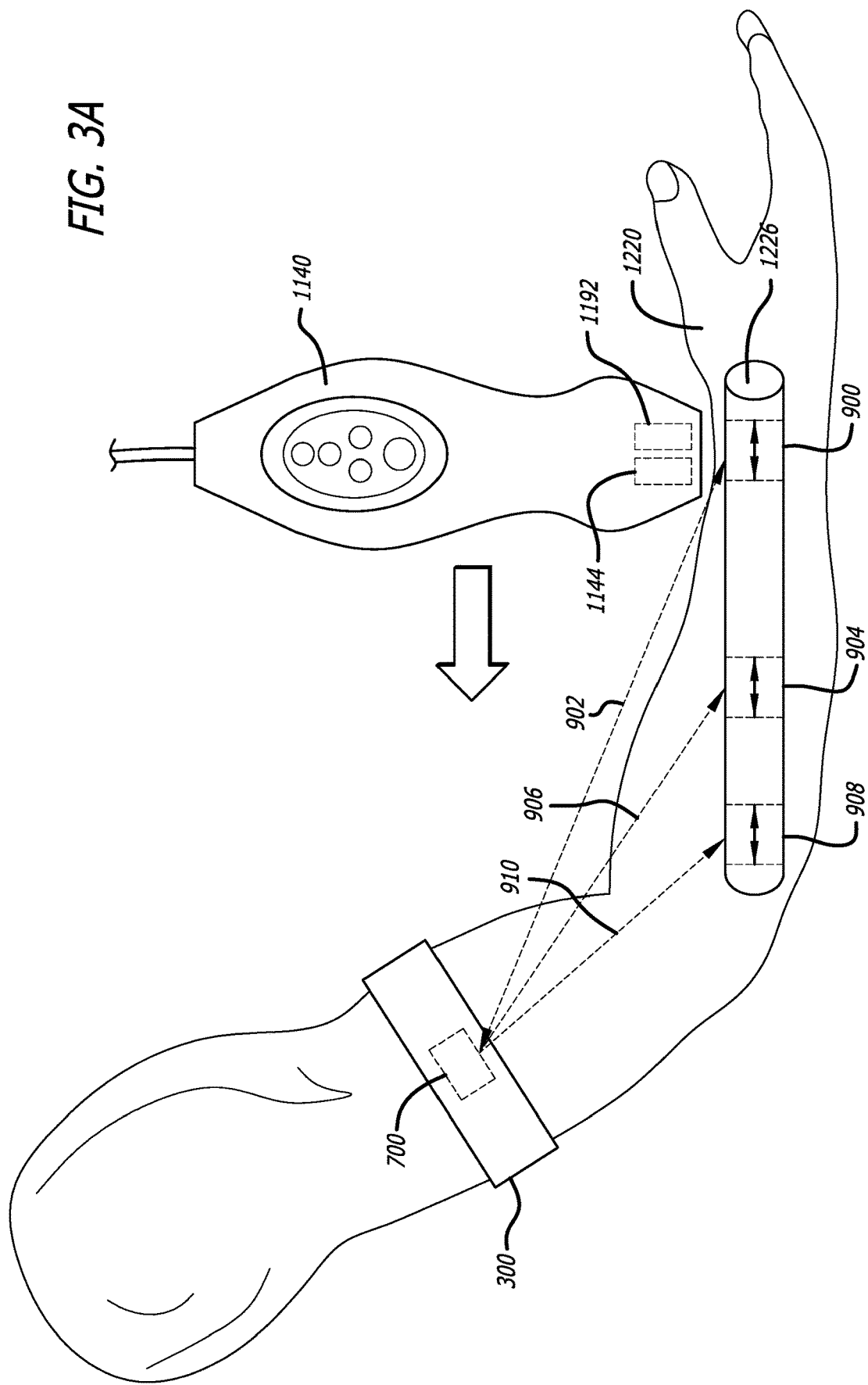

SYSTEM, METHOD AND APPARATUS FOR MAGNETIC TRACKING OF ULTRASOUND PROBE AND GENERATION OF 3D VISUALIZATION THEREOF

PRIORITY

This application claims the benefit of priority to U.S. Provisional Application No. 63/054,622, filed Jul. 21, 2020, which is incorporated by reference in its entirety into this application.

SUMMARY

Briefly summarized, embodiments disclosed herein are directed to systems, methods, and devices for magnetic tracking of ultrasound probes and use of the magnetic tracking of ultrasound probes to generate 3D visualization of target vessels.

Blood vessel cannulation can be difficult in some patients. One problem that often arises with blood vessel cannulation is difficulty in visualizing the target vessel and other details important for cannulation including vessel movement, vessel size, depth, proximity to unintended structures or even impediments within the target vessel including valves, stenosis, thrombosis etc.

In some embodiments, a magnetic-based tracking system for tracking an ultrasound probe to create a three-dimensional (3D) visualization includes a reference device including a reference magnet; an ultrasound probe including a magnetometer configured to detect a magnetic field generated by the reference magnet, wherein the ultrasound probe is configured to couple a first ultrasound image with a first magnetic field strength, and wherein the first ultrasound image is received at a first time, and the first magnetic field strength is detected at the first time. The system further includes a console including a processor and non-transitory computer-readable medium having stored thereon a plurality of logic modules that, when executed by the processor, are configured to perform operations including receiving a plurality of couplings of ultrasound images and detected magnetic field strengths, recording the plurality of couplings of ultrasound images and detected magnetic field strengths, and generating the 3D visualization from the ultrasound images by aligning each of the ultrasound images in accordance with a corresponding detected magnetic field strength.

In some embodiments, the magnetic based tracking system includes where the reference device is a cuff like structure that wraps around a body segment to be imaged.

In some embodiments, the magnetic based tracking system includes where the reference device is a U-shaped structure and is configured to allow the body segment to be placed within the U-shaped structure for imaging.

Also disclosed is a magnetic based tracking system for tracking an ultrasound probe to create a three-dimensional (3D) visualization, including a reference device including a magnetometer that detects a magnetic field generated by a reference magnet and creates a timestamp for a magnetic field strength reading; an ultrasound probe including an ultrasound acoustic transducer or acoustic array that acquires ultrasound images and creates a timestamp for each specific ultrasound image, and a reference magnet that is configured to generate a magnetic field. The system also includes a console including a processor and non-transitory computer-readable medium having stored thereon a plurality of logic modules that, when executed by the processor, are configured to perform operations including receiving a plurality of ultrasound images and detected magnetic field strengths, coupling a plurality of ultrasound images and detected magnetic field strengths by their timestamps, recording the plurality of couplings of ultrasound images and detected magnetic field strengths, and generating the 3D visualization from the ultrasound images by aligning each of the ultrasound images in accordance with a corresponding detected magnetic field strength.

In some embodiments, the magnetic based tracking system includes where the reference device is a cuff like structure that wraps around a body segment to be imaged.

In some embodiments, the magnetic based tracking system includes where the reference device is a U-shaped structure and is configured to allow the body segment to be placed within the U-shaped structure for imaging.

Also disclosed is a method of creating a 3D image using a magnetic based tracking system for tracking an ultrasound probe including configuring the reference device around the body segment to be imaged; advancing ultrasound probe on skin surface of the body segment to be imaged; capturing time stamped ultrasound images while simultaneously detecting time stamped magnetic field strength of a reference magnet by magnetometer; determining distance between reference magnet and magnetometer; and stitching together ultrasound images using magnetic field strength data and time stamps to create a 3D image.

In some embodiments, the method includes where configuring the reference device includes the reference device being a cuff like structure and including a reference magnet.

In some embodiments, the method includes where advancing the ultrasound probe includes the ultrasound probe including a magnetometer.

In some embodiments, the method includes where configuring the reference device includes the reference device being a U-shaped structure and is configured to allow the bodily appendage to be placed within the U-shaped structure for imaging.

In some embodiments, the method includes where the stitching together the ultrasound images includes using only the magnetic field strength data.

In some embodiments, the method includes where configuring the reference device includes the reference device being a cuff-like structure and including the magnetometer.

In some embodiments, the method includes where advancing the ultrasound probe includes the ultrasound probe including the reference magnet.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 3A illustrates a side view of the magnetic-based tracking system including the ultrasound probe of FIG. 2A according to some embodiments;

DETAILED DESCRIPTION

Figure 1:
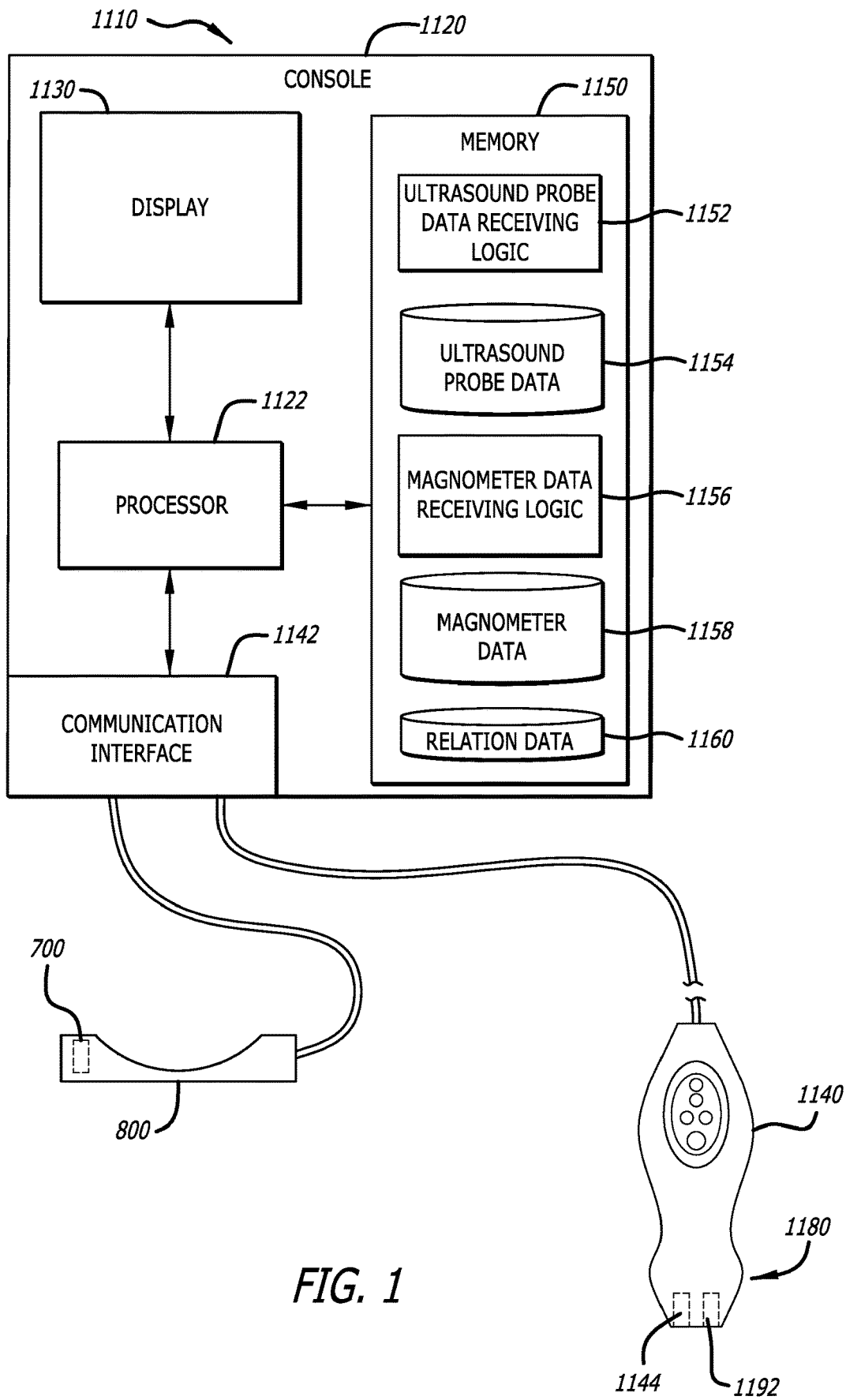
FIG. 1 illustrates a block diagram depicting various elements of a magnetic-based tracking system for an ultrasound probe and other medical components to create a 3D image according to some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Referring to FIG. 1, a block diagram depicting various elements of a magnetic-based tracking system 1110 for tracking of an ultrasound probe 1140 and generation of a three-dimensional (3D) image is shown in accordance with one example embodiment of the present invention. As shown, the system 1110 generally includes a console 1120, an ultrasound probe 1140, and a reference-device 800, where each of the probe 1140 and the reference device 800 are configured to be communicatively coupled to the console 1120. The console 1120 is shown to include one or more processors 1122, a communication interface 1142, a display 1130 and non-transitory, computer-readable medium ("memory") 1150. The memory 1150 is configured to store logic modules including an ultrasound probe data receiving logic 1152 and a magnetometer data receiving logic 1156. Further, the memory 1150 may include data stores such as the ultrasound probe data 1154, magnetometer data 1158 and the relation data 1160.

In some embodiments, the processor 1122, including non-volatile memory such as EEPROM for instance, is included in the console 1120 for controlling system function during operation of the system 1110, thus acting as a control processor. The display 1130 in the present embodiment may be integrated into the console 1120 and is used to display information to the clinician while using the ultrasound probe 1140. In another embodiment, the display 1130 may be separate from the console 1120.

The ultrasound probe 1140 uses an ultrasound acoustic transducer or acoustic array to produce and receive echoes that can be converted into an image. For example, in some embodiments, the ultrasound probe may include an ultrasound generation device including an ultrasound acoustic stack or other various modalities of ultrasound generation (e.g., microelectromechanical systems (MEMS) based, etc.). Within the magnetic-based tracking system, in some embodiments, the ultrasound probe 1140 may additionally include a magnetometer for measuring a magnetic field strength. In some embodiments, the ultrasound probe 1140 may include a reference magnet.

The reference device 800 is a device that, in some embodiments, contains the reference magnet 700 of the magnetic-based tracking system 1110. In some embodiments, the reference device 800 may be a cuff-like structure that contains the reference magnet 700 and wraps around a body segment (e.g., bodily appendage, torso, mid-section, chest, etc.) to be imaged. In other embodiments, the reference device 800 may include a U-shaped structure that contains the reference magnet 700 and is configured to allow the bodily appendage to be placed within the U-shaped structure for imaging. In other embodiments, the reference device 800 may include a magnetometer.

Figure 2A:
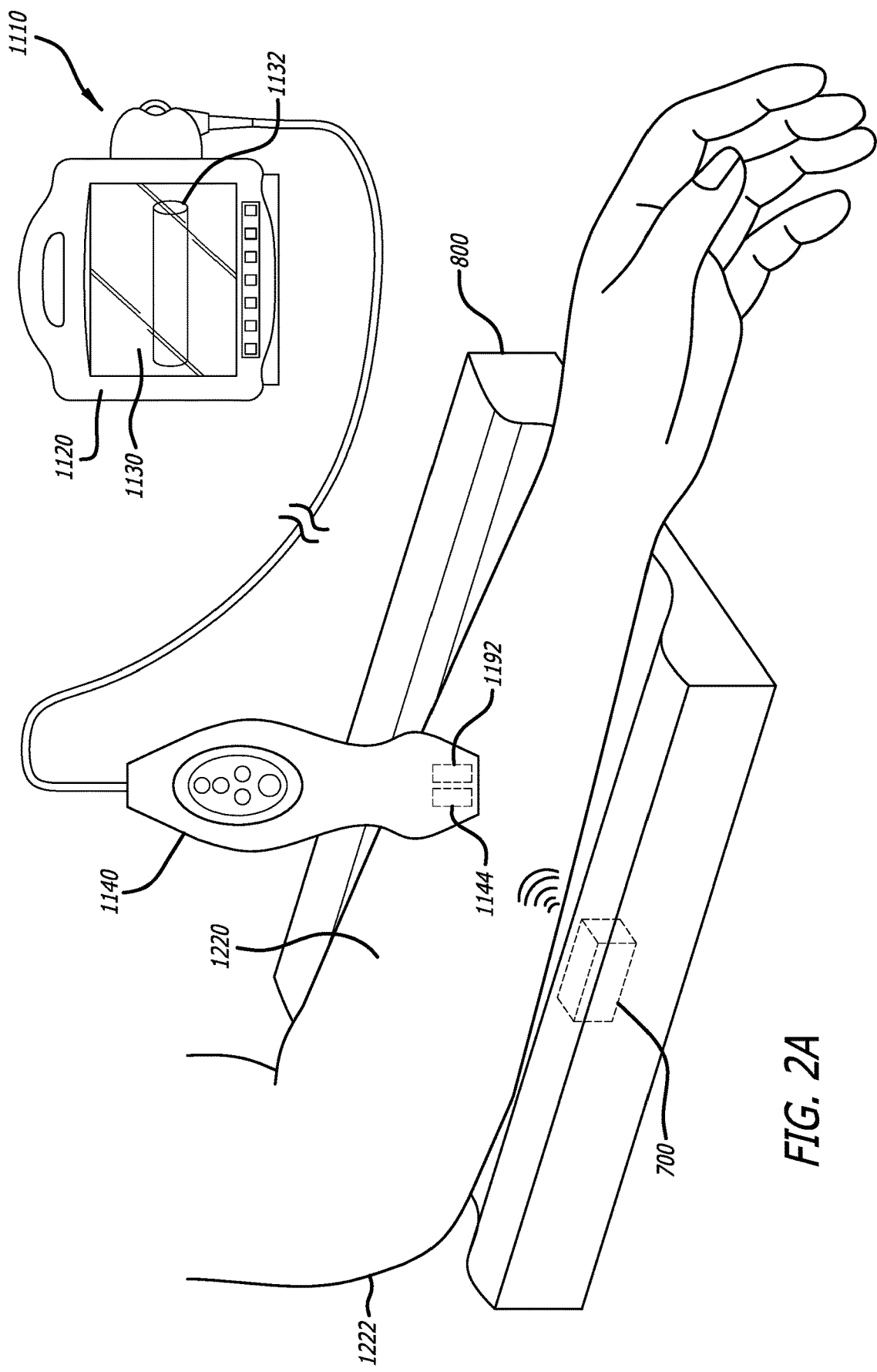
FIG. 2A illustrates a top view of the magnetic-based tracking system including the ultrasound probe of FIG. 1 according to some embodiments.

FIG. 2A illustrates a top view of the magnetic-based tracking system 1110 including the ultrasound probe 1140 of FIG. 1 according to some embodiments. The ultrasound probe 1140 is employed in connection with the reference device 800 in order to track the positioning of the probe 1140 as it is moved about a surface of a patient. As shown, the probe 1140 is configured to be moved along a surface (i.e., skin) 1220 of a bodily appendage 1222 of a patient. The reference device 800 may be deployed within a threshold distance to the bodily appendage 1222. In some embodiments, the reference device 800 may comprise a hard, plastic casing configured in a "U-shape" such as shown in FIG. 1, where an interior is formed by the convex portion of the configuration. In such an instance, the bodily appendage 1222 (e.g., an arm) may be placed within the interior.

The magnetic-based tracking system 1110 can be used, in some embodiments, in preparation for insertion of the needle and/or catheter into the vasculature. Specifically, the system 1110 employs the combination of the probe 1140 and the reference device 800 to track the positioning of the probe 1140 in relation to a reference magnet 700 of the reference device 800. By tracking the positioning of the probe 1140 in relation to the reference magnet 700, the system 1110 is able to relate each ultrasound image obtained by the probe 1140 to a positioning of the probe 1140 on the bodily appendage 1222. By relating an ultrasound image to a positioning on the appendage 1222, the system 1110 may then stitch together the set of ultrasound images to form a 3D visualization of the bodily appendage 1222. Such a 3D visualization gives real-time 3D ultrasound guidance and assists in reducing complications typically associated with such introduction, including inadvertent arterial puncture, hematoma, pneumothorax, etc.

In some embodiments, the ultrasound probe 1140 includes a head 1180 that houses an ultrasound acoustic transducer or acoustic array 1144 for producing ultrasonic pulses and for receiving echoes thereof after reflection by the patient's body when the head is placed against the patient's skin 1220, wherein each echo may be converted into an image. The ultrasound acoustic transducer or acoustic array 1144 may be in operable communication with the console 1120 for storing ultrasound images. In some embodiments, the ultrasound probe 1140 includes a sensor component, such as the magnetometer 1192, for detecting the position of the reference magnet 700 during ultrasound imaging procedures, such as those described above. As will be described in further detail below, the magnetometer 1192 may be embedded within the head 1180 of the ultrasound probe 1140. The magnetometer 1192 is configured to detect a magnetic field associated with the reference magnet 700 and enable the system 1110 to track the reference magnet 700 as it relates to the magnetometer 1192. In the present embodiment, the magnetometer 1192 is disposed in a planar configuration in the head 1180 of the ultrasound probe 1140, though it is appreciated that the magnetometer 1192 can be disposed in other configurations within the ultrasound probe 1140. The magnetometer 1192 may exist in a paired longitudinal configuration with the ultrasound acoustic transducer or acoustic array 1144. In other embodiments, the magnetometer 1192 may exist in a paired latitudinal configuration, paired circular configuration or a combination thereof with the ultrasound acoustic transducer or acoustic array 1144.

In some embodiments, the magnetometer 1192 may include a series of magnetometers arranged in a configuration to track the reference magnet 700. In one embodiment, the magnetometer 1192 includes three orthogonal sensor coils for enabling detection of a magnetic field in three spatial dimensions (not shown). An example of a 3D magnetic sensor is one manufactured by Honeywell Sensing and Control of Morristown, NJ Further, the magnetometer 1192 in one embodiment are configured as Hall-effect sensors, though other types of magnetic sensors could be employed.

The magnetometer 1192 may be in communication with the console 1120 for storing information about the position of the magnetometer 1192 in relation to the reference magnet 700, which will be described in more detail herein.

Figure 2B:
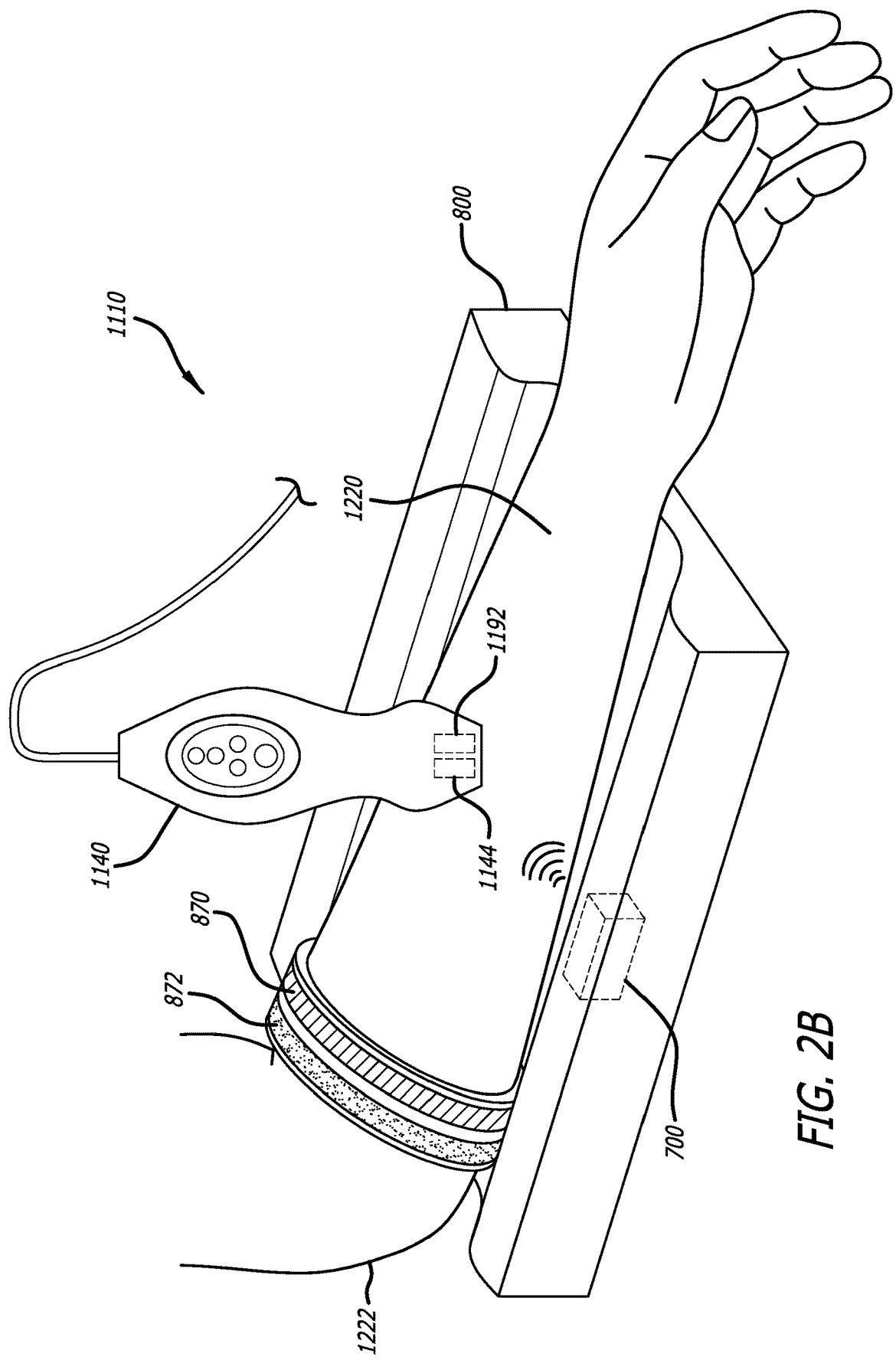
FIG. 2B illustrates a top view of a magnetic-based tracking system including a remote-control tourniquet, a remote-control heating element and the ultrasound probe of FIG. 1 according to some embodiments.

In some embodiments, as illustrated in FIGS. 2A and 2B, the reference magnet 700 generates a magnetic field that can be detected and measured using the magnetometer 1192. As the ultrasound probe 1140 is moved along the surface 1220 of the bodily appendage 1222, the strength of the magnetic field as detected by the magnetometer 1192 changes. The detected strength of the magnetic field is recorded along with an ultrasound image captured by the probe 1140, where both are transmitted to the console 1120 for storage and processing, which may include generation of a 3D image comprised of a plurality of ultrasound images. In some embodiments, the reference magnet 700 includes an electromagnet that is coupled to a power supply (not shown). In such an embodiment, the strength of the magnetic field can be increased which allows the ultrasound probe 1140 to be used at greater distances from the reference magnet 700.

FIG. 2A shows the bodily appendage 1222 that is cradled within the interior of the reference device 800. It can be appreciated that the bodily appendage 1222 can be any bodily appendage and further understood that reference-devices having various sizes may be deployed with the system 1110 (i.e., to enable the system to be used with different appendages). In some embodiments, reference devices may be specifically configured for use with specific appendages (e.g., arms, legs) or other body portions (e.g., torso). In addition, some references devices may be specifically configured for use with children while others are configured for use with adults, where adult-sized reference devices generally have a larger size than those configured for children). In some embodiments, the bodily appendage 1222 may include but is not limited to a lower arm, an upper arm, a lower leg, an upper leg, or a foot.

In some embodiments, the reference device 800 may be configured to fit body segments such as a torso, multiple legs, or multiple arms. In some embodiments, the reference device 800 may be reusable and may be made of durable material such as nylon, other polyesters or harden plastics. In some embodiments as illustrated in FIG. 2A, the reference device 800 may be configured to surround multiple sides of a bodily appendage, wherein bodily appendage 1222 may be inserted through the open side of the reference device 800 with the appendage 1222 unobstructed for imaging.

As will be described in more detail below, the inclusion of the reference magnet 700 and the magnetometer 1192 in the system 1110 provides numerous advantages over current ultrasound systems, specifically with respect to generation of visualizations based on the obtained ultrasound data. Briefly, the reference magnet 700 generates a magnetic field that is detectable by the magnetometer 1192 in the ultrasound probe 1140. As the reference magnet 700 remains stationary relative to the patient's appendage during use of the ultrasound probe 1140, the reference magnet 700 acts as a reference point for the ultrasound probe 1140. Thus, the ultrasound probe 1140 may be specifically configured to associate a detected magnetic field strength with a particular ultrasound image (received as an echo). Further, the ultrasound probe 1140 may be configured to continuously associate a strength of a detected magnetic field with an obtained ultrasound image. The associated pairings of {detected magnetic field strength, ultrasound image} may be provided to the console 1130 such that the logic of which may generate a 3D visualization 1132 by stitching the ultrasound images together based on the magnetic field strength associated with each. In other words, the logic of the console 1130 may properly align the ultrasound images based on the detected magnetic field strength associated with each. In particular, the detected magnetic field strength provides an indication of a location on the patient's appendage in relation to the stationary reference magnet 700, which is used to align the ultrasound images.

In one particular embodiment, the reference device 800 may fully surround the bodily appendage 1222, for example, a sleeve-like structure that completely encloses the bodily appendage 1222 to be imaged. In such an embodiment, the reference device 800 may be constructed of a cloth, neoprene or mesh material and may be affixed in position by sliding the reference device 800 over the appendage 1222 to be imaged. In some embodiments, the reference device 800 may be configured to surround and be secured to the bodily appendage 1222 to be imaged. For example, the reference device 800 may wrap completely around the upper arm, proximal the elbow and be secured to the upper arm by a first piece of temporary adhesive such as double-sided tape or Velcro (see FIG. 3A).

In some embodiments, as illustrated in FIG. 2B, the reference device 800 may be in communication with a remote-controlled tourniquet 870 to compress the bodily appendage 1222, and a remote-controlled heating element 872 to engorge blood vessels during use.

Referring to FIG. 3A, a side view of the magnetic-based tracking system 1110 including the ultrasound probe 1140 of FIG. 2 is shown according to some embodiments. In some embodiments, as the ultrasound probe 1140 is moving on the surface of the skin 1220, the ultrasound acoustic transducer or acoustic array 1144 is capturing images while the magnetometer 1192 measures the strength of a detected magnetic field as generated by the reference magnet 700 and relays the magnetic field strength information back to the console 1120 along with the captured ultrasound image. In other words, as the ultrasound probe 1140 is moved along a patient's bodily appendage, the ultrasound probe 1140 transmits an ultrasonic pulse and receives an echo, which is translated into information utilized to render a two-dimensional (2D) image of the echo received at a particular location on the bodily appendage. As disclosed herein, as the ultrasound probe 1140 transmits the ultrasonic pulse and receives the echo, the magnetometer 1192 concurrently detects a magnetic field generated by the reference magnet 700 and records its strength, where concurrently means at least partially overlapping in time. Thus, the ultrasound probe 1140 captures information for creating a 2D ultrasound image at a particular location along the bodily appendage and records the strength of the magnetic field detected at that location. The ultrasound information and the magnetic field strength are coupled and transmitted to the console 1110 for storage and processing. For instance, a plurality of ultrasound information and magnetic field strength couplings may be used to create a 3D visualization of at least a portion of the bodily appendage by stitching 2D images created from the ultrasound information together based the magnetic field strength data. Specifically, the magnetic field strength data may be used to align the 2D ultrasound images based on a reference point (e.g., the location of the reference magnet 700) through analysis of the magnetic field strength data.

As illustrated in FIG. 3A, the ultrasound probe 1140 takes a first ultrasound image 900 of the blood vessel 1226 using the ultrasound acoustic transducer or acoustic array 1144 while the magnetometer 1192 records a first strength 902 of the detected magnetic field generated by the reference magnet 700. The ultrasound probe 1140 takes a second ultrasound image 904 of the blood vessel 1226 using the ultrasound acoustic transducer or acoustic array 1144 while the magnetometer 1192 records a second strength 906 of the detected magnetic field generated by the reference magnet 700. Further, the ultrasound probe 1140 takes a third ultrasound image 908 of the blood vessel 1226 using the ultrasound acoustic transducer or acoustic array 1144 while the magnetometer 1192 records a third strength 910 of the detected magnetic field generated by the reference magnet 700. The first image 900 and first strength 902, the second image 904 and second strength 906, and the third image 908 and third strength 910 are each coupled and sent to the console 1120 for storage and processing. Specifically, the console 1120 may create or add to a database of {ultrasound image, magnetic field strength} pairs. The database can then be used to construct a 3D image in a way that will be described in more detail herein.

Figure 3B:
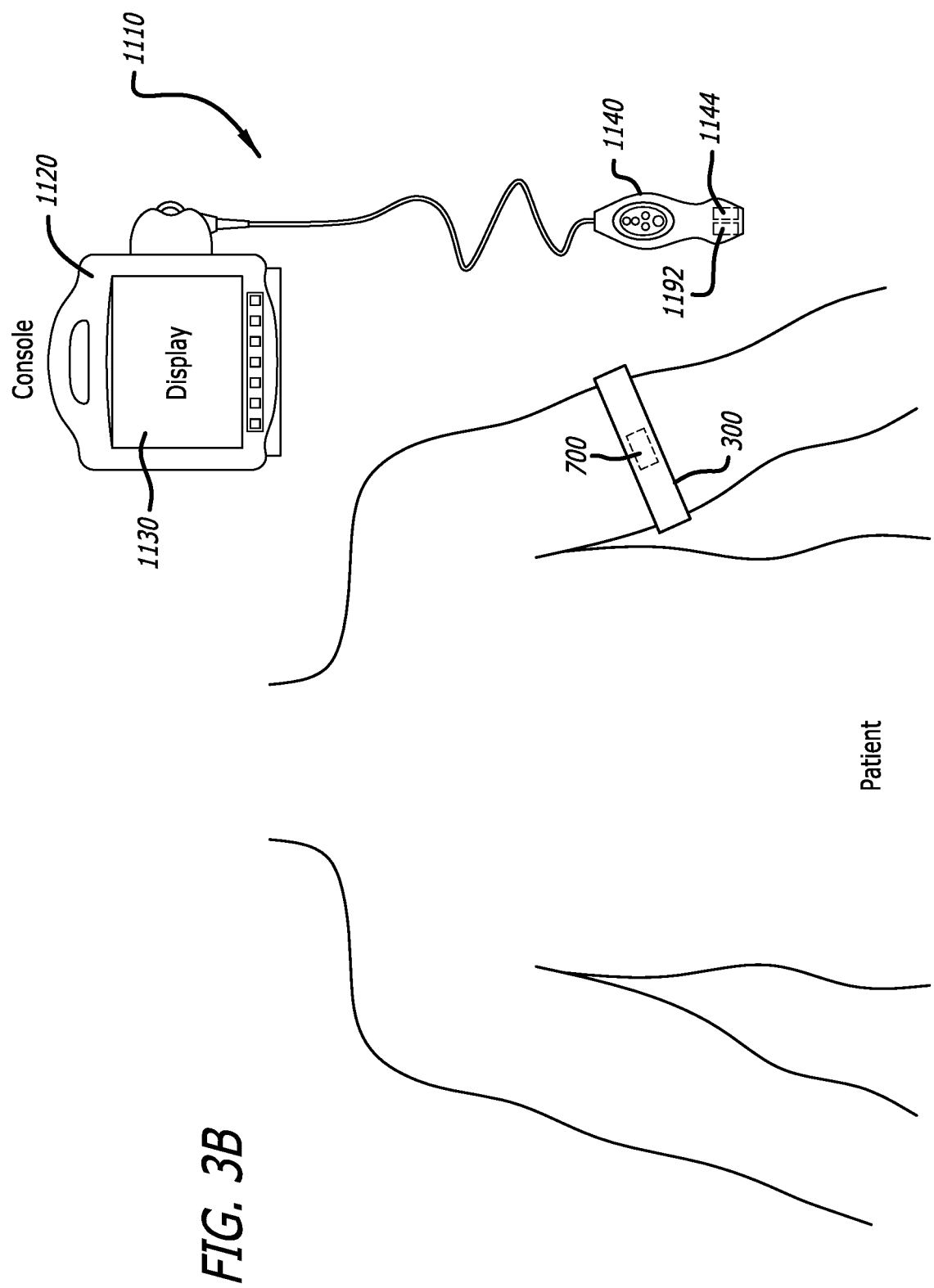
FIG. 3B illustrates a front view of the magnetic-based tracking system including the ultrasound probe and console of FIG. 2A according to some embodiments.

FIG. 3B provides an illustration of an alternative embodiment to the reference device 800 as illustrated in FIGS. 1-2. For example, in FIGS. 1-2, the reference device 800 is illustrated as a cuff-like device wherein a bodily appendage may be received at an interior of the reference device 800. In contrast, the reference device 300 of FIG. 3B is illustrated as a wearable device, e.g., an arm band, in which the reference magnetic 700 is incorporated. It should be understood that the various embodiments of reference devices discussed in FIGS. 1-5 are interchangeable in the functionality described, especially with respect to associating a captured ultrasound image with a detected magnetic field strength.

As mentioned above, the system 1110 in the present embodiment may be configured to detect the position and movement of the ultrasound probe 1140. In particular, the magnetometer 1192 in the probe 1140 is configured to detect a magnetic field generated by or otherwise associated with the reference magnet 700. In some embodiments, when the magnetometer 1192 includes multiple magnetometers, each of the magnetometers may be configured to spatially detect the magnetic field in three-dimensional space. Thus, during operation of the system 1110, the magnetic field strength data of the reference magnet 700 sensed by each of the magnetometers 1192 is forwarded to a processor, such as the processor 1122 of the console 1120 (FIG. 1), which, in conjunction with logic, such as the magnetometer data receiving logic 1156 of the console 1120 (FIG. 1) computes, in real-time, the position of the ultrasound probe 1140 in relation to the reference magnet 700 as well as the distance between the reference magnet 700 and the ultrasound probe 1140.

Figure 4:
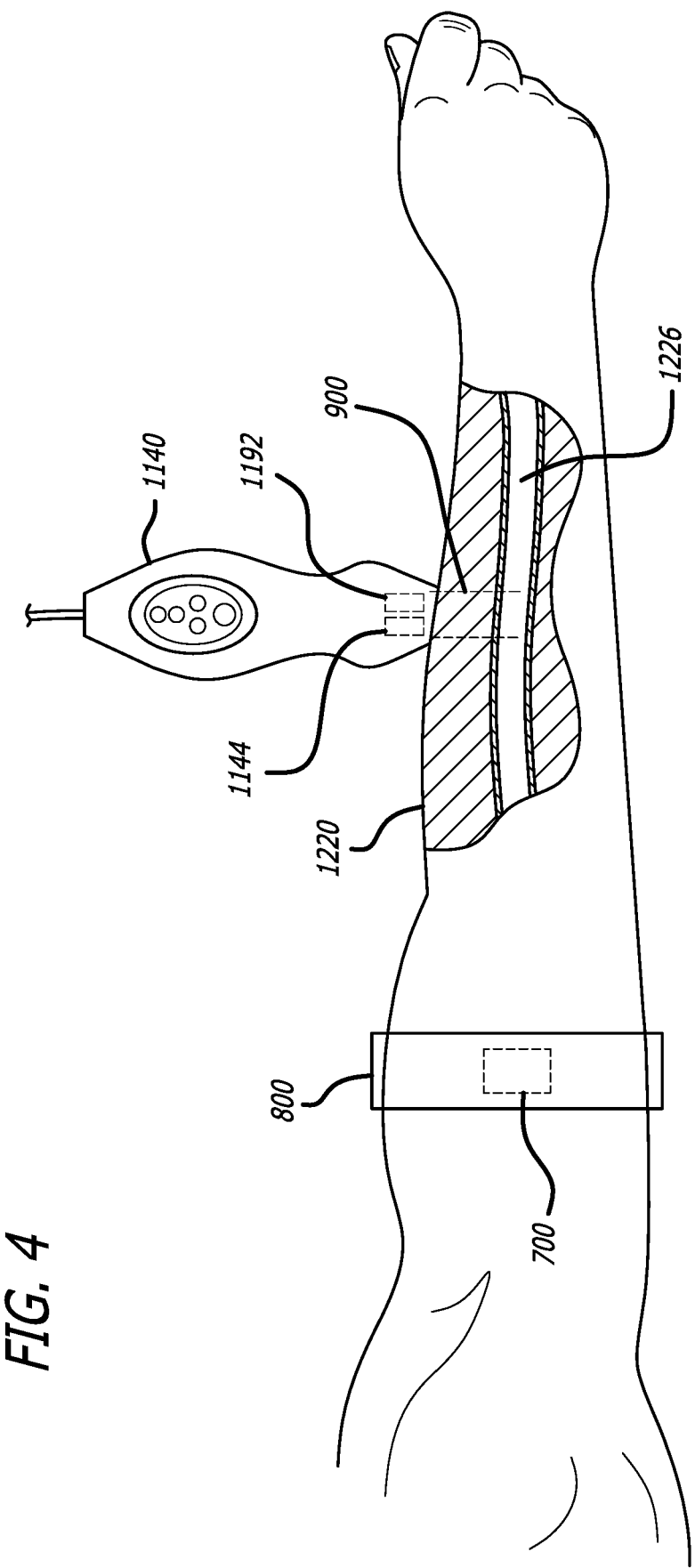
FIG. 4 illustrates a side view of the magnetic based tracking system including the ultrasound probe of FIG. 3 according to some embodiments.

FIG. 4 illustrates a side view of the magnetic based tracking system 1110 including the ultrasound probe 1140 of FIG. 3A according to some embodiments. In various embodiments, the reference magnet 700 within the reference device 800 can be configured at different places in relation to the magnetometer 1192 and the ultrasound probe 1140. For example, in a first embodiment, the reference magnet 700 may be located in line with the ultrasound probe 1140 or, in a second embodiment as is illustrated in FIG. 4, the reference magnet 700 may be located out of line with the ultrasound probe 1140.

Figure 5:
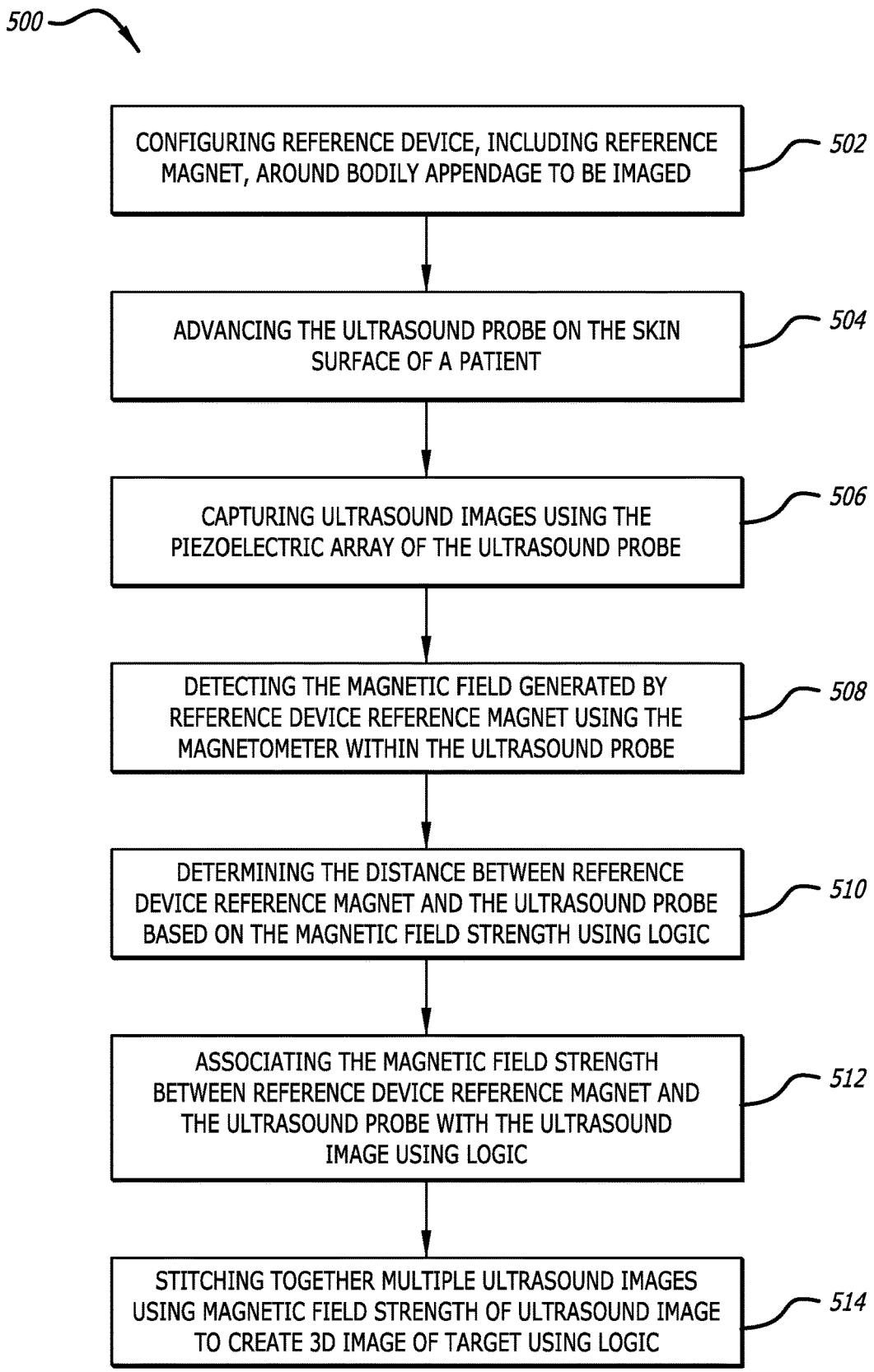
FIG. 5 is a flowchart illustrating an exemplary method for using a magnetic-based tracking system for an ultrasound probe of FIG. 1 to create a 3D image according to some embodiments.

Referring to FIG. 5, a flowchart illustrating an exemplary method for creating a 3D image using a magnetic-based tracking system of FIG. 1 is shown according to some embodiments. Each block illustrated in FIG. 5 represents an operation performed in the method 500 of creating a 3D image using the magnetic-based tracking system of FIG. 1. Prior to detecting the proximity of the reference magnet to the magnetometer in the probe, in one embodiment, is assumed that the magnetic-based tracking system includes a probe having a body and a magnetometer, and the reference magnet in a reference device that has been configured to generate a magnetic field. It is further assumed that the magnetometer is configured to detect the magnetic field generated by the reference magnet. Finally, it is assumed that the magnetic-based tracking system includes logic that is stored on non-transitory computer-readable medium and, when executed by one or more processors, causes performance of operations associated with the proximity detection disclosed herein.

As an initial step in the method 500, the reference device is configured around the bodily appendage to be imaged (block 502). As is understood, the reference device may fully or partially surround the bodily appendage to be imaged. In some embodiments, the reference device may be fixed to the bodily appendage and may be placed above or below the bodily appendage for enhanced imaging.

The ultrasound probe is advanced on the skin surface of a patient to image a target vessel (block 504). As is understood, the probe may be positioned on the skin surface enabling the projection of an ultrasound beam toward the target vessel for imaging purposes (see FIG. 4). In some embodiments, the advancing step includes advancing the ultrasound probe in any direction on the surface of the skin.

As the ultrasound probe is advanced toward the target vessel, the ultrasound acoustic transducer or acoustic array within the head of the probe captures images of the target vessel (block 506). In some embodiments, the capturing step includes capturing the ultrasound images to a database located on the console.

Simultaneously, the magnetometer of the probe detects a magnetic field strength generated by or associated with the reference magnet that is included in the reference device (block 508). In some embodiments, when the magnetometer includes multiple magnetometers, the detecting step includes using all the magnetometers to detect the magnetic field.

The logic determines a distance between the reference magnet and the magnetometer of the probe based at least in part on the magnetic field strength (block 510). As discussed above, the logic may be stored on a console, the probe or an alternative electronic device. In some embodiments, when the magnetometer includes multiple magnetometers, the logic may determine the distance using the distance from each magnetometer.

Once the magnetic field strength between the reference magnet and the magnetometer of the probe is determined, the data is configured into a database that associates the distance between the reference magnet and the magnetometer with the ultrasound image recorded at the exact distance (block 512). In some embodiments, when the magnetometer includes multiple magnetometers, the distance data from each magnetometer can be configured to be stored into the database.

Finally, in response to associating the magnetic field strength between the reference magnet and magnetometer with the ultrasound image recorded at that exact distance, the logic stitches together multiple ultrasound images using the magnetic field strength associated with each specific image to stitch the images together sequentially (block 514). The stitching together of the multiple ultrasound images provides a 3D image of the target.

Figure 6:
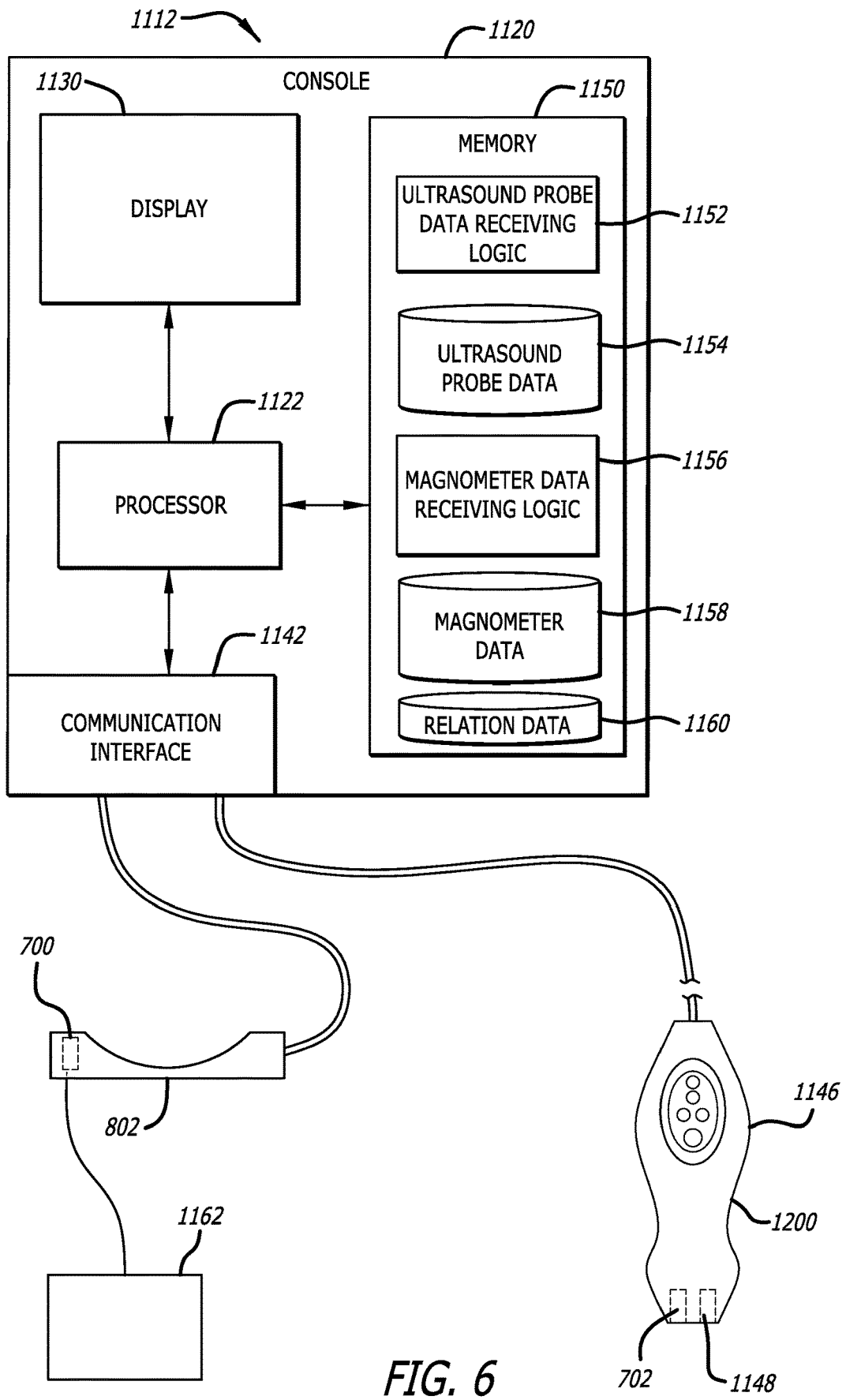
FIG. 6 illustrates a block diagram depicting various elements of a magnetic-based tracking system for an ultrasound probe and other medical components to create a 3D image according to some embodiments.

Referring to FIG. 6, a block diagram depicting various elements of a magnetic-based tracking system 1112 for tracking of an ultrasound probe 1146 and generation of a three-dimensional (3D) image is shown in accordance with one example embodiment of the present invention. As shown, the system 1112 generally includes a console 1120, an ultrasound probe 1146, and a reference-device 802, where each of the probe 1146 and the reference device 802 are configured to be communicatively coupled to the console 1120. The console 1120 is shown to include one or more processors 1122, a communication interface 1142, a display 1130 and non-transitory, computer-readable medium ("memory") 1150. The memory 1150 is configured to store logic modules including a magnetometer data receiving logic 1156 and an ultrasound probe data receiving logic 1152. Further, the memory 1150 may include data stores such as the magnetometer data 1158, ultrasound probe data 1154, and the relation data 1160. In some embodiments, the logic currently in the console 1120 will perform the association of the time stamp from the ultrasound images data with the time stamps from the magnetic field strength data. The time stamps for the ultrasound images and the time stamps for the magnetic field strength data may be included in other embodiments discussed herein, including for the purpose of confirming the ultrasound image and magnetic field strength association in the event of a transmission error from the ultrasound probe 1146 and reference device 802 to the console 1120.

In some embodiments, the processor 1122, including non-volatile memory such as EEPROM for instance, is included in the console 1120 for controlling system function during operation of the system 1110, thus acting as a control processor. The display 1130 in the present embodiment may be integrated into the console 1120 and is used to display information to the clinician while using the ultrasound probe 1140. In another embodiment, the display 1130 may be separate from the console 1120.

In some embodiments, as illustrated in FIG. 6, the reference device 802 includes the magnetometer 1194 and a power source 1162 to power the magnetometer 1194. In some embodiments, the ultrasound probe 1146 includes the ultrasound acoustic transducer or acoustic array 1148 and a reference magnet 702 that can be configured in the head 1182 of the ultrasound probe 1146. The magnetometer 1194 as shown in FIG. 6 performs in a similar manner as discussed above with respect to magnetometer 1192 of FIGS. 1-4. However, the magnetometer 1194 of FIG. 6 is incorporated into the reference device 802 where the reference device 802 having the magnetometer 1192 detects a reference magnet 702 strength data and transmits such to the console 1120. The reference magnet 702 as shown in FIG. 6 performs in a similar manner as discussed above with respect to reference magnet 700 of FIGS. 1-4. However, the reference magnet 702 of FIG. 6 is incorporated into the ultrasound probe 1146, where the ultrasound probe 1146 does not collect the magnetic field strength data.

In some embodiments, the magnetic-based tracking system 1112 includes the reference device 802 further including the magnetometer 1194 and the ultrasound probe 1146 including the reference magnet 702 wherein the reference magnet 702 can be attached to the ultrasound probe 1146 via a sleeve around a probe handle 1200 or otherwise attached. This embodiment allows the reference magnet 702 to be used with various ultrasound probes that do not include reference magnets configured inside the head 1182 of the ultrasound probe 1146.

Figure 7:
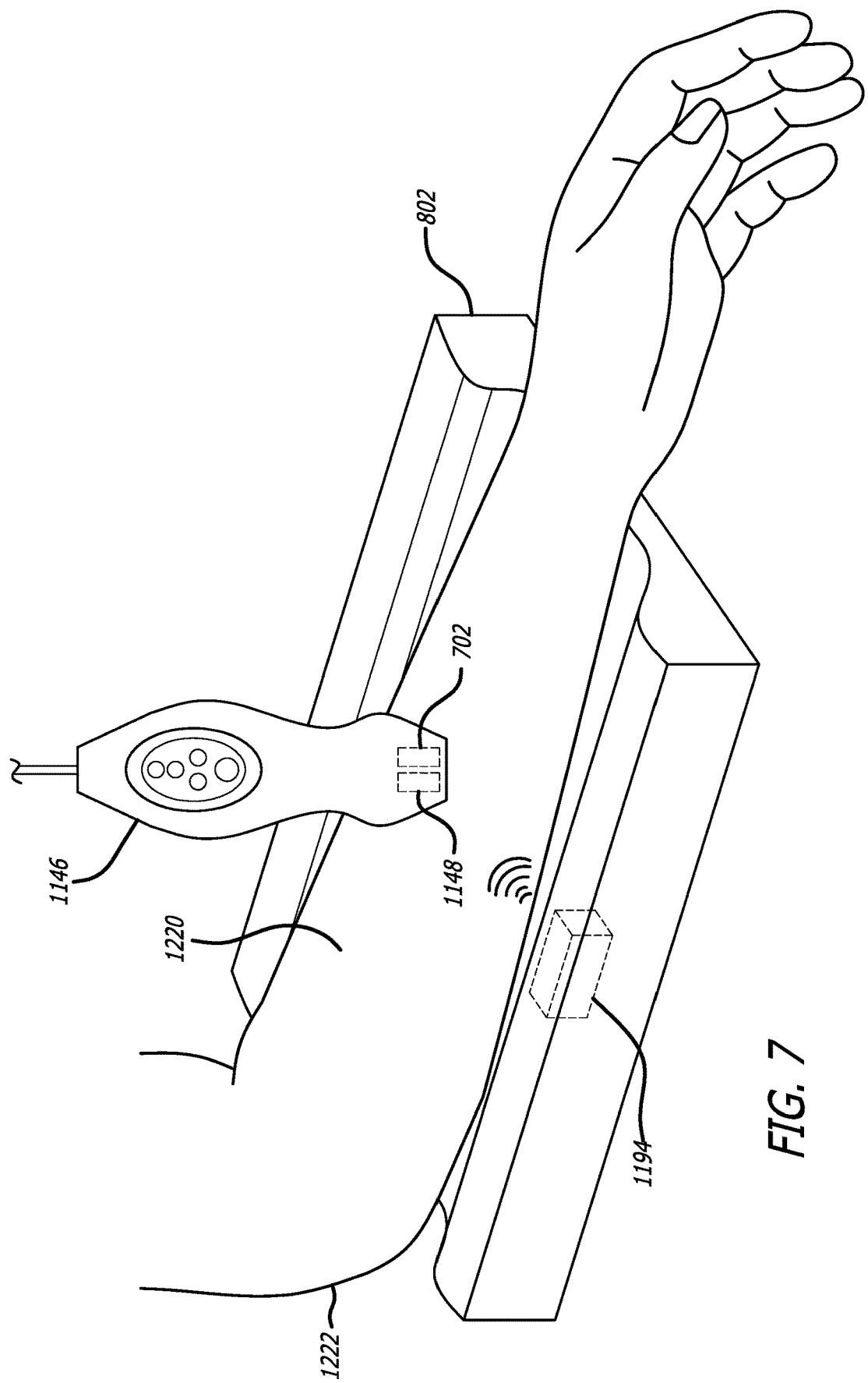
FIG. 7 illustrates a top view of the magnetic-based tracking system including the ultrasound probe of FIG. 6 according to some embodiments.

FIG. 7 illustrates a top view of the magnetic-based tracking system 1112 including the ultrasound probe 1146 of FIG. 6 according to some embodiments. The ultrasound probe 1146 is employed in connection with the reference device 802 in order to track the positioning of the ultrasound probe 1146 as it is moved about a skin surface of a patient 1220. As shown, the probe 1146 is configured to be moved along the surface (i.e., skin) 1220 of a bodily appendage 1222 of a patient. The reference device 802 may be deployed within a threshold distance to the bodily appendage 1222. In some embodiments, the reference device 802 may comprise a hard, plastic casing configured in a "U-shape" such as shown in FIG. 6, where an interior is formed by the convex portion of the configuration. In such an instance, the bodily appendage 1222 (e.g., an arm) may be placed within the interior.

The magnetic-based tracking system 1112 can be used, in some embodiments, in preparation for insertion of the needle and/or catheter into the vasculature. Specifically, the system 1112 employs the combination of the probe 1146, the reference device 802 including the magnetometer 1194 to track the positioning of the ultrasound probe 1146 in relation to a reference magnet 702 within the ultrasound probe 1146. By tracking the positioning of the probe 1146 in relation to the reference magnet 702, the system 1112 is able to relate each ultrasound image obtained by the probe 1146 to a positioning of the probe 1146 on the bodily appendage 1222. By relating an ultrasound image to a positioning on the appendage 1222, the system 1112 may then stitch together the set of ultrasound images to form a 3D visualization of the bodily appendage 1222. Such a 3D visualization gives real-time 3D ultrasound guidance and assists in reducing complications typically associated with such introduction, including inadvertent arterial puncture, hematoma, pneumothorax, etc.

In some embodiments, the ultrasound probe 1146 includes a head 1182 that houses an ultrasound acoustic transducer or acoustic array 1148 for producing ultrasonic pulses and for receiving echoes thereof after reflection by the patient's body when the head 1182 is placed against the patient's skin 1220, wherein each echo may be converted into an image. The ultrasound acoustic transducer or acoustic array 1148 may be in operable communication with the console 1120 for storing ultrasound images. In some embodiments, the ultrasound probe 1146 includes a reference magnet 702 for providing the position of the ultrasound probe 1146 during ultrasound imaging procedures, such as those described above. As will be described in further detail below, the reference magnet 702 may be embedded within the head 1182 of the ultrasound probe 1146. In the present embodiment, the reference magnet 702 is disposed in a planar configuration in the head 1182 of the ultrasound probe 1146, though it is appreciated that the reference magnet 702 can be disposed in other configurations within the ultrasound probe 1146. The reference magnet 702 may exist in a paired longitudinal configuration, paired latitude configuration, paired circular configuration or a combination thereof with the ultrasound acoustic transducer or acoustic array 1148.

In some embodiments, the magnetometer 1194 may include a series of magnetometers arranged in a configuration to track the reference magnet 702. In one embodiment, the magnetometer 1192 includes three orthogonal sensor coils for enabling detection of a magnetic field in three spatial dimensions (not shown). An example of a 3D magnetic sensor is one manufactured by Honeywell Sensing and Control of Morristown, NJ Further, the magnetometer 1192 in one embodiment are configured as Hall-effect sensors, though other types of magnetic sensors could be employed.

The magnetometer 1194 may be in communication with the console 1120 for storing information about the position of the reference magnet 702 in relation to the magnetometer 1194, which will be described in more detail herein.

The magnetometer 1194 is configured to detect a magnetic field associated with the reference magnet 702 and enable the system 1112 to track the reference magnet 702 as it relates to the magnetometer 1194.

Figure 8:
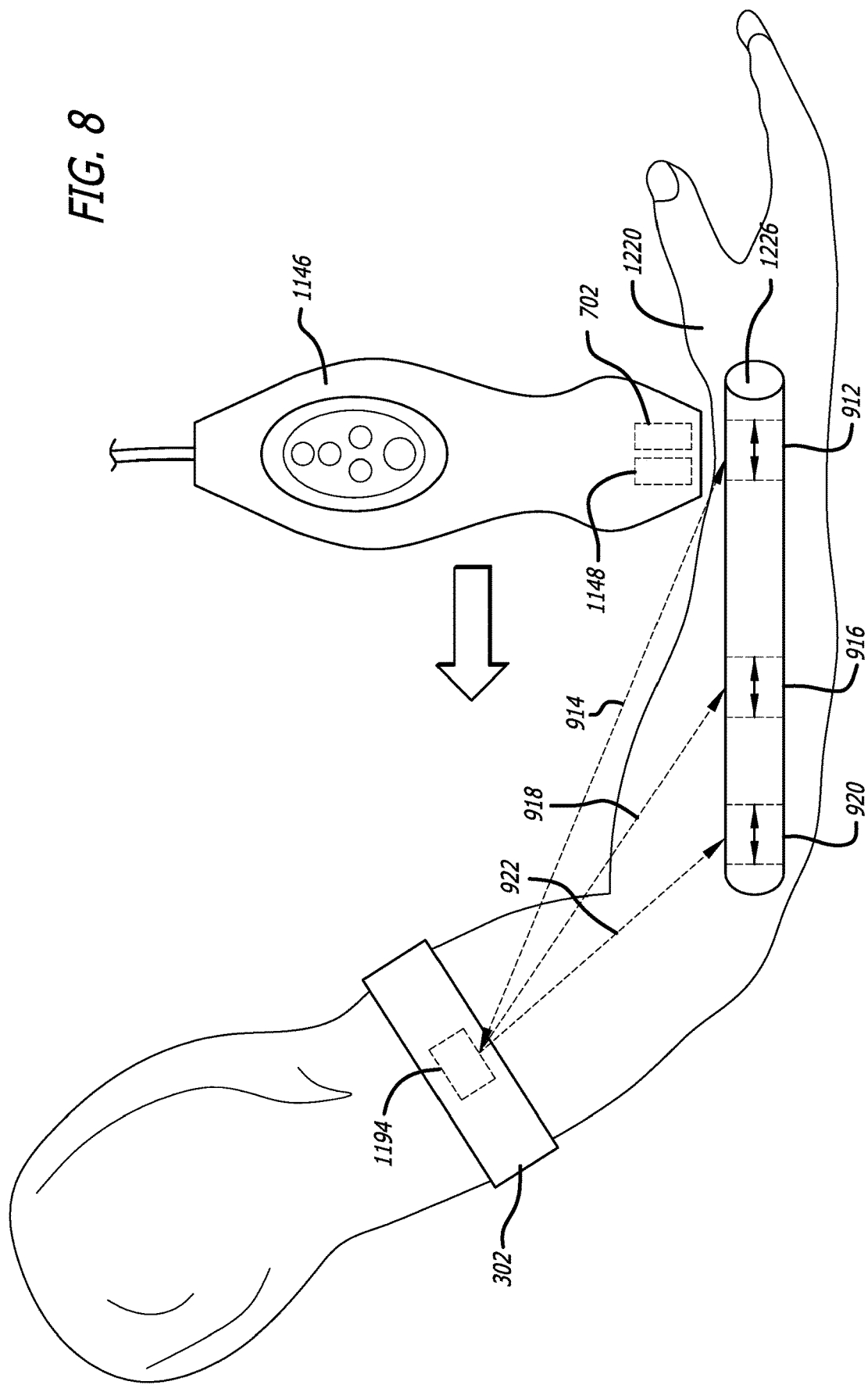
FIG. 8 illustrates a side view of the magnetic-based tracking system including the ultrasound probe of FIG. 7 according to some embodiments.

Referring to FIG. 8, a side view of the magnetic-based tracking system 1112 including the ultrasound probe 1146 of FIG. 7 is shown according to some embodiments. In some embodiments, as the ultrasound probe 1146 is moving on the surface of the skin 1220, the ultrasound acoustic transducer or acoustic array 1148 is capturing images while the magnetometer 1194 in the reference device 802 measures the strength of a detected magnetic field as generated by the reference magnet 702 in the ultrasound probe 1146 and relays the magnetic field strength information back to the console 1120 along with the captured ultrasound image.

In other words, as the ultrasound probe 1194 is moved along a patient's bodily appendage, the ultrasound probe 1146 transmits an ultrasonic pulse and receives an echo, which is translated into information and time stamped, utilized to render a two-dimensional (2D) image of the echo received at a particular location on the bodily appendage. As disclosed herein, as the ultrasound probe 1146 transmits the ultrasonic pulse and receives the echo, the magnetometer 1194 within the reference device 802 concurrently detects a magnetic field generated by the reference magnet 702 within the ultrasound probe 1146 and records its strength and time stamps the magnetic field strength, where concurrently means at least partially overlapping in time. Thus, the ultrasound probe 1146 captures information for creating a 2D ultrasound image at a particular location along the bodily appendage and the magnetometer 1194 records the strength of the magnetic field detected at that location. The ultrasound information including the time stamp and the magnetic field strength and time stamp are coupled and transmitted to the console 1110 for storage and processing. For instance, a plurality of ultrasound information, magnetic field strength and time stamp couplings may be used to create a 3D visualization of at least a portion of the bodily appendage by stitching 2D images created from the ultrasound information together based the magnetic field strength data and time stamping. Specifically, the magnetic field strength data and concurrent time stamp may be used to align the 2D ultrasound images based on a reference point (e.g., the location of the reference magnet 702) through analysis of the magnetic field strength data.

As illustrated in FIG. 8, the ultrasound probe 1146 takes a first ultrasound image 912 of the blood vessel 1226 using the ultrasound acoustic transducer or acoustic array 1148 that is time stamped while the magnetometer 1194 in the reference device 802 records a first strength 914 that is time stamped of the detected magnetic field generated by the reference magnet 702 within the ultrasound probe 1146. The ultrasound probe 1146 takes a second ultrasound image 916 of the blood vessel 1226 using the ultrasound acoustic transducer or acoustic array 1148 that is time stamped while the magnetometer 1194 records a second strength 918 that is time stamped of the detected magnetic field generated by the reference magnet 702. Further, the ultrasound probe 1146 takes a third ultrasound image 920 of the blood vessel 1226 using the ultrasound acoustic transducer or acoustic array 1148 that is time stamped while the magnetometer 1194 records a third strength 922 that is time stamped of the detected magnetic field generated by the reference magnet 702. The first image 912 and first strength 914, the second image 916 and second strength 918, and the third image 920 and third strength 922 are each coupled and sent to the console 1120 for storage and processing. Specifically, the console 1120 may create or add to a database of {(ultrasound image, time stamp) (magnetic field strength, time stamp)} pairs. The database can then be used to construct a 3D image in a way that will be described in more detail herein.

Figure 9:
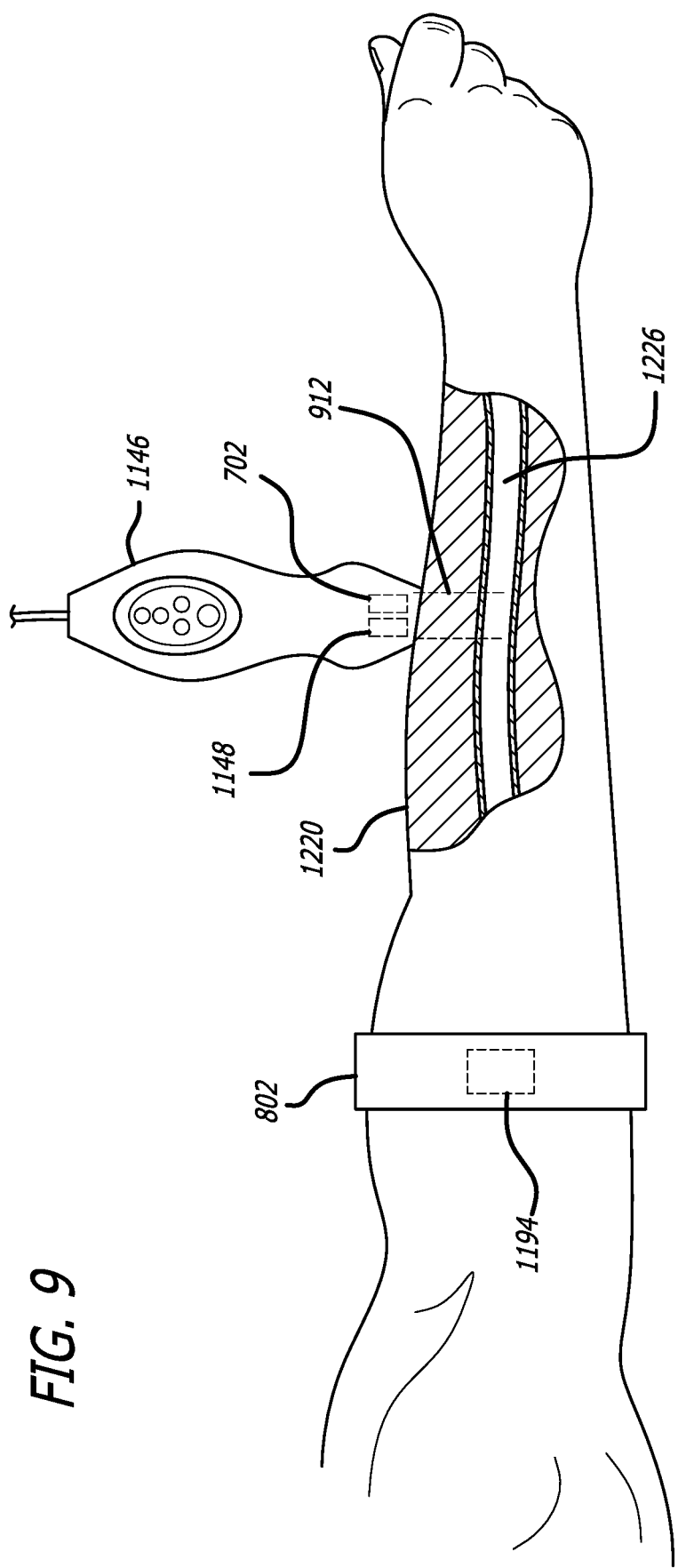
FIG. 9 illustrates a side view of the magnetic based tracking system including the ultrasound probe of FIG. 8 according to some embodiments.

FIG. 9 illustrates a side view of the magnetic based tracking system 1112 including the ultrasound probe 1146 and reference device 802 of FIG. 8 according to some embodiments. The magnetometer 1194 within the reference device 802 can be configured at multiple places in relation to the reference magnet 702 and the ultrasound probe 1146. For example, the magnetometer 1194 may be located in line with the ultrasound probe 1146 and reference magnet 702 or the magnetometer 1194 may be located out of line with the ultrasound probe 1146 and reference magnet 702 as illustrated in FIG. 4.

Figure 10:
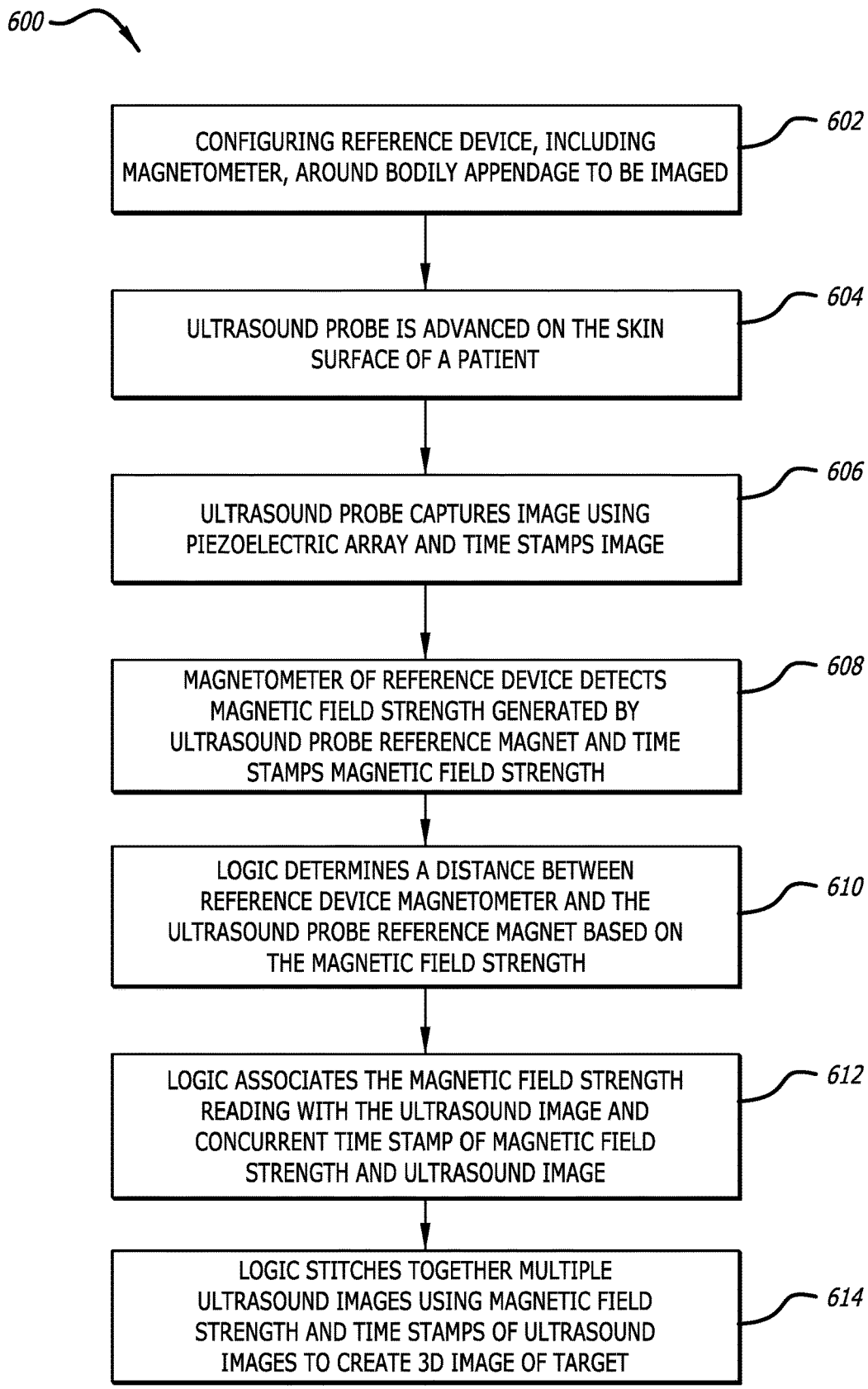
FIG. 10 is a flowchart illustrating an exemplary method for using a magnetic-based tracking system for an ultrasound probe of FIG. 6 to create a 3D image according to some embodiments.

Referring to FIG. 10, a flowchart illustrating an exemplary method 600 for creating a 3D image using a magnetic-based tracking system 1112 of FIG. 6 is shown according to some embodiments. Each block illustrated in FIG. 10 represents an operation performed in the method 1000 of creating a 3D image using the magnetic-based tracking system of FIG. 6. Prior to detecting the proximity of the reference magnet in the ultrasound probe to the magnetometer in the reference device, in one embodiment, is assumed that the magnetic-based tracking system includes a probe having a body and a reference magnet configured to generate a magnetic field, and the magnetometer in a reference device that has been configured to detect the magnetic field generated by the reference magnet. Finally, it is assumed that the magnetic-based tracking system includes logic that is stored on non-transitory computer-readable medium and, when executed by one or more processors, causes performance of operations associated with the proximity detection disclosed herein.

As an initial step in the method 600, the reference device is configured around the bodily appendage to be imaged (block 602). As is understood, the reference device may fully or partially surround the bodily appendage to be imaged. In some embodiments, the reference device may be fixed to the bodily appendage and may be placed above or below the bodily appendage for enhanced imaging.

The ultrasound probe is advanced on the skin surface of a patient to image a target vessel 1226 (block 604). As is understood, the probe may be positioned on the skin surface enabling the projection of an ultrasound beam toward the target vessel for imaging purposes (see FIG. 9). In some embodiments, the advancing step includes advancing the ultrasound probe in any direction on the surface of the skin.

As the ultrasound probe is advanced toward the target vessel, the ultrasound acoustic transducer or acoustic array within the head of the probe captures images of the target vessel (block 606). In some embodiments, the capturing step includes capturing the ultrasound images to a database located on the console.

Simultaneously, the magnetometer of the reference device detects a magnetic field strength generated by or associated with the reference magnet that is included in or on the ultrasound probe (block 608). In some embodiments, when the magnetometer includes multiple magnetometers, the detecting step includes using all the magnetometers to detect the magnetic field.

The logic determines a distance between the reference magnet of the probe and the magnetometer of the reference device based at least in part on the magnetic field strength (block 610). As discussed above, the logic may be stored on a console, the probe or an alternative electronic device. In some embodiments, when the magnetometer includes multiple magnetometers, the logic may determine the distance using the distance from each magnetometer.

Once the magnetic field strength between the reference magnet of the probe and the magnetometer of the reference device is determined, the data is configured into a database that associates the distance between the reference magnet and the magnetometer with the ultrasound image recorded at the exact distance and the time stamp of the ultrasound image and the time stamp of the magnetic field strength (block 612). In some embodiments, when the magnetometer includes multiple magnetometers, the distance data from each magnetometer can be configured to be stored into the database.

Finally, in response to associating the magnetic field strength between the reference magnet and magnetometer with the ultrasound image recorded at that exact distance, the logic stitches together multiple ultrasound images using the magnetic field strength associated with each specific image and the time stamps to stitch the images together sequentially (block 614). The stitching together of the multiple ultrasound images provides a 3D image of the target.

In addition to the above described embodiments, the inventive concepts may also be utilized in further embodiments such as, but not limited to, those described below. For example, in one embodiment, the tracking structure of the magnetometer, the reference magnet and ultrasound probe are used to provide 31) views/guidance of anatomical structures intended for access with a needle (e.g. nerve blocks, drainage sites, biopsy sites, etc.).

In another embodiment, the combination the tracking structure and a needle tracking system is used to capture the trajectory of the needle in 3D. In furtherance of such an embodiment, the system 1110 may record of the path of the needle to the target structure (e.g. center of vessel, nerve bundle, drainage site, pneumothorax, etc.). In yet another embodiment, a magnetic or electromagnetic needle guidance system is used to visually track within the 3D scan.

In another embodiment, the 3D scan may be viewed by a clinician through a virtual, augmented or mixed-reality system. In furtherance of such an embodiment, the clinician can evaluate or track needles, wires or tools in real time.

In some embodiments, the tracking structure could be combined with vessel ID methods and Doppler capabilities to map veins and arteries observed during the scanning process.

In another embodiment, the tracking structure could be combined with a hands-free ultrasound probe to enable a live image at the desired insertion location and a 3D pre-scanned image. The hands-free probe with the combination of the tracking structure would allow the clinician to use both hands for procedural device manipulation of the needle and patient interaction of skin stabilization or limb extension simultaneously.

In some embodiments, the remote-controlled tourniquet may be a separate cuff from the reference device 800. In some embodiments, the remote-controlled heating element may be a separate cuff from the reference device 800.

In another embodiment, the tracking structure, in conjunction with the ultrasound, could be used to create a baseline image of the lungs and a post-procedure scan to identify changes in the lungs (e.g. sliding lung behavior associated with pneumothorax or improved blood flow). In furtherance of such an embodiment, this combination could be combined with additional methods to identify or highlight structures of interest such as nerve bundles in the 3D scans.

In another embodiment, the tracking structure could include radio-opaque markers pursuant to the correlation to or image combination with X-ray, fluoroscopy or a combination thereof.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A magnetic-based tracking system for tracking an ultrasound probe to create a three dimensional (3D) visualization, the system comprising:
   a reference device including a reference magnet;
   the ultrasound probe comprising a magnetometer, wherein the ultrasound probe is configured to capture ultrasound images, wherein the magnetometer is configured to detect magnetic field strengths of a magnetic field generated by the reference magnet, and wherein a position of the ultrasound probe is tracked on a portion of a patient body in relation to the reference magnet;
   and a console including a processor and non-transitory computer-readable medium having stored thereon logic that, when executed by the processor, is configured to perform operations including;
   receiving the ultrasound images, the magnetic field strengths, and corresponding timestamps for both the ultrasound images and the magnetic field strengths;
   pairing the ultrasound images with the magnetic field strengths based on corresponding timestamps for both the ultrasound images and the magnetic field strengths;
   and generating the 3D visualization of the portion of the patient body from the ultrasound images by (i) aligning each of the ultrasound images in accordance with ultrasound image-magnetic field strength pairings and (ii) stitching the ultrasound images together in relation to the position of the ultrasound probe on the portion of the patient body.

2. The magnetic-based tracking system according to claim 1, wherein the reference device is a cuff-like structure that wraps around a body segment to be imaged.

3. The magnetic-based tracking system according to claim 2, wherein the reference device is a U-shaped structure and is configured to allow the body segment to be placed within the U-shaped structure for imaging.

4. The magnetic-based tracking system according to claim 1, further comprising: a needle tracking system configured to capture a trajectory of a needle in three-dimensions, wherein the needle tracking system is configured to record a path of the needle to a target structure of the portion of the patient body captured by the ultrasound probe.

5. The magnetic-based tracking system according to claim 4, wherein the target structure is one of a vessel center, a nerve bundle, a drainage site, or a pneumothorax.

6. The magnetic-based tracking system according to claim 1, further comprising; a magnetic or electromagnetic needle guidance system configured to track a path of a needle to a target structure of the portion of the patient body captured by the ultrasound probe.

7. The magnetic-based tracking system according to claim 1, wherein the 3D visualization is rendered via a virtual, augmented or mixed-reality system.

8. The magnetic-based tracking system according to claim 1, further comprising:
   a vessel identification system; and
   a Doppler system, wherein the vessel identification system and the Doppler system are configured to map one or more veins or one or more arteries.

9. The magnetic-based tracking system according to claim 1, wherein the ultrasound probe is a hands-free ultrasound probe.

10. The magnetic-based tracking system according to claim 1, further comprising:
    a remote-controlled tourniquet configured to compress the portion of the body segment being imaged by the ultrasound probe.

11. The magnetic-based tracking system according to claim 1, further comprising a remote-controlled heating element configured to engorge blood vessels.

\* \* \* \* \*